(12) United States Patent
Kimura

(10) Patent No.: US 10,192,028 B2
(45) Date of Patent: Jan. 29, 2019

(54) DATA ANALYSIS DEVICE AND METHOD THEREFOR

(71) Applicant: HITACHI HIGH-TECHNOLOGIES CORPORATION, Tokyo (JP)

(72) Inventor: Kouichi Kimura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 482 days.

(21) Appl. No.: 14/762,897

(22) PCT Filed: Nov. 20, 2013

(86) PCT No.: PCT/JP2013/081233
§ 371 (c)(1),
(2) Date: Jul. 23, 2015

(87) PCT Pub. No.: WO2014/132497
PCT Pub. Date: Sep. 4, 2014

(65) Prior Publication Data
US 2015/0363549 A1    Dec. 17, 2015

(30) Foreign Application Priority Data

Feb. 28, 2013  (JP) ................................. 2013-038919

(51) Int. Cl.
*G06F 17/30* (2006.01)
*G06F 19/22* (2011.01)
*G06F 19/28* (2011.01)

(52) U.S. Cl.
CPC ........ *G06F 19/22* (2013.01); *G06F 17/30507* (2013.01); *G06F 17/30528* (2013.01); *G06F 19/28* (2013.01)

(58) Field of Classification Search
CPC .......... G06F 19/22; G06F 19/24; G06F 19/28; G06F 17/30528; G06F 17/30507
(Continued)

(56) References Cited

U.S. PATENT DOCUMENTS 8,788,522 B2 *   7/2014  Kimura ........................ 707/770
9,522,217 B2    12/2016  Kutryk et al.
(Continued)

FOREIGN PATENT DOCUMENTS

| CN | 1922325 A | 2/2007 |
| CN | 102363051 A | 2/2012 |
| JP | 2003-330934 A | 11/2003 |

OTHER PUBLICATIONS

Extended European Search Report received in corresponding European Application No. 13876221.6 dated Sep. 8, 2016.
(Continued)

*Primary Examiner* — Jean B Fleurantin
(74) *Attorney, Agent, or Firm* — Mattingly & Malur, PC

(57) ABSTRACT

The computational cost for a mapping process performed in analyzing genome/exome/transcriptome is reduced by sorting all cyclic permutations or suffixes of all read sequences to allow a search to be performed on the basis of any base sequence as a key. Also performed is computing and storing, for each base position in a genome sequence, the minimum length for uniqueness (MLU) at which a partial sequence starting from the base position becomes unique in the genome. In analysis of variations, a target region is scanned to inspect the number of matching read sequences that contain a partial sequence with a length of MLU and thus estimate the position of a variation, and then, the read sequences are collected at a position where the possibility of a variation having occurred is high to perform comparison analysis of the sequences.

18 Claims, 19 Drawing Sheets

(58) Field of Classification Search
USPC .......................................................... 707/769
See application file for complete search history.

(56) References Cited

U.S. PATENT DOCUMENTS

| | | | |
|---|---|---|---|
| 2005/0164198 A1 | 7/2005 | Imai et al. | |
| 2010/0286925 A1 | 11/2010 | Halpern et al. | |
| 2012/0041977 A1* | 2/2012 | Kimura | G06F 17/30985 707/772 |
| 2016/0186192 A1 | 6/2016 | Finnis et al. | |

OTHER PUBLICATIONS

Chinese Office Action received in corresponding Chinese Application No. 201380071119.1 dated Dec. 26, 2016.

M. Burrows et al., A block-sorting Lossless Data Compression Algorithm. Technical Report 124, Research Report 124, May 10, 1994.

Heng Li et al., Fast and accurate short read alignment with Burrows-Wheeler Transform. Bioinformatics, 2009, pp. 1754-1760. vol. 25, No. 14.

Aaron McKenna et al., The Genome Analysis Toolkit: a MapReduce framework for analyzing next-generation DNA sequencing data, Genome Res. 2010 20: 1297-303.

Sabrina Mantaci et al., An extension of the Burrows Wheeler transform to k words, Data Compression Conference, 2005. Proceedings. DCC 2005.

Markus J. Bauer et al., Light-weight BWT Construction for Very Large String Collections, Combinatorial Pattern Matching, Lecture Notes in Computer Sciencevol. 6661, 2011, pp. 219-231.

Paolo Ferraginaet al., Light-weight Data Indexing and Compression in External Memory, Algorithmica, Jul. 2012, vol. 63, Issue 3, pp. 707-730.

Kouichi Kimura et al., Computation of rank and select functions on hierarchical binary string and its application to genome mapping problems for short-read DNA sequences, Journal of Computational Biology, 2009, pp. 1601-1613 vol. 16, No. 11.

Ge Nong et al., Linear Suffix Array Construction by Almost Pure Induced-Sorting, Data Compression Conference, 2009.

International Search Report of PCT/JP2013/081233.

* cited by examiner

Fig. 18

Formula 1

$\begin{cases} G\text{: Reference Genome Sequence (Both Strands)} \\ \quad G = C_1 + \$ + C_2 + \$ + \cdots + \$ + C_I + \$ + C_1^t + \$ + \cdots + C_I^t + \$ \\ \qquad C_i\text{: Base Sequence of i-th Chromosome (Character String Composed of A,C,G,T,N)} \\ \qquad \text{(where } 1 \leq i \leq I) \\ \qquad C_i^t\text{: Complementary Sequence of } C_i \\ \qquad I\text{: Number of Chromosomes} \\ \qquad \$\text{: Delimiter} \\ \qquad +\text{: Concatenation of Character Strings} \\ G[x, y]\text{: Partial Sequence of G whose Base Position Coordinate is Greater than or Equal to} \\ x \text{ and Less than or Equal to } y \\ Occ(w, G)\text{: Number of Times Base Sequence w Appears as Partial Sequence of G (Number} \\ \text{of Appearances)} \\ R\text{: Character String Obtained by Concatenating All Read Sequences with Delimiters } \$ \\ \quad R = r_1 + \$ + r_2 + \$ + \cdots + \$ + r_J + \$ \\ \qquad r_j\text{: Base Sequence of j-th Read Sequence } (1 \leq j \leq J) \\ \qquad J\text{: Number of Read Sequences} \\ Occ(w, R)\text{: Number of Times Base Sequence w Appears as Partial Sequence of R (Number} \\ \text{of Appearances)} \end{cases}$ Formula 2

$\begin{cases} N(x, \ell) = Occ(G[x, x + \ell - 1], G) \\ L(x) = \text{Min}\{ \ell \mid N(x, \ell) \leq 1 \} : \quad \text{MLU at x (Forward Direction)} \\ D(x) = Occ(G[x, x + L(x) - 1], R) : \quad \text{Depth at x (Forward Direction)} \end{cases}$ Formula 3

$\begin{cases} N(x, \ell) = Occ(G[x - \ell + 1, x], G) \\ L(x) = \text{Min}\{ \ell \mid N(x, \ell) \leq 1 \} : \quad \text{MLU at x (Backward Direction)} \\ D(x) = Occ(G[x - L(x) + 1, x], R) : \quad \text{Depth at x (Backward Direction)} \end{cases}$

Fig. 19

Formula 4

$$\underbrace{\$\$...\$}_{n(\$)\text{ Pieces}}\underbrace{AA...A}_{n(A)\text{ Pieces}}\underbrace{CC...C}_{n(C)\text{ Pieces}}\underbrace{GG...G}_{n(G)\text{ Pieces}}\underbrace{TT...T}_{n(T)\text{ Pieces}}\underbrace{NN...N}_{n(N)\text{ Pieces}}$$

Formula 5

$$n = n(\$) + n(A) + n(C) + n(G) + n(T) + n(N)$$

Formula 6

$$Q(\$) = \underbrace{AA...A}_{n(A)\text{ Pieces}}\underbrace{CC...C}_{n(C)\text{ Pieces}}\underbrace{GG...G}_{n(G)\text{ Pieces}}\underbrace{TT...T}_{n(T)\text{ Pieces}}\underbrace{NN...N}_{n(N)\text{ Pieces}}$$

Formula 7

$$\underbrace{\$\$...\$}_{q(\$,y)\text{ Pieces}}\underbrace{AA...A}_{q(A,y)\text{ Pieces}}\underbrace{CC...C}_{q(C,y)\text{ Pieces}}\underbrace{GG...G}_{q(G,y)\text{ Pieces}}\underbrace{TT...T}_{q(T,y)\text{ Pieces}}\underbrace{NN...N}_{q(N,y)\text{ Pieces}}$$

DATA ANALYSIS DEVICE AND METHOD THEREFOR

TECHNICAL FIELD

The present invention relates to a data analysis device for a DNA sequence, and in particular, to a technique of analyzing DNA sequence data obtained from a massively parallel DNA sequencing device.

BACKGROUND ART

For treatment of cancers, lifestyle-related diseases, genetic diseases, and the like, it is necessary to inspect the genetic backgrounds of individual patients to select suitable treatment or predict prognoses for them, as so-called individualized medicine. Therefore, DNA (deoxyribonucleic acid) sequences, such as the genome or transcriptome, are analyzed. A DNA sequencing device used therefor is able to obtain only a short, fragmented DNA sequence. Therefore, it is necessary to perform data processing for inspecting from which part of the genome the obtained fragmented sequence derives by comparing it with a very long reference genome sequence, and further inspecting the presence or absence of variations, such as SNP (Single Nucleotide Polymorphisms), insertion, or deletion, contained in the sequence. Such data processing is typically called a mapping process.

When a massively parallel DNA sequencer called next-generation DNA sequencer is used, hundreds of millions of fragmented sequences (read sequences) each having a length of about 100 bases, which is relatively short, are obtained in a single measurement. When a human is a test subject, a reference genome sequence used therefor is as long as about 3 giga bases (3 billion bases). In a mapping process, such read sequences are compared with the reference genome sequence one by one to identify the corresponding positions and identify variations contained therein. As such a process requires a huge computational cost, dedicated, efficient algorithms have been developed and used. A representative method includes creating a database of a reference genome sequence through BWT (Burrows-Wheeler Transformation) (see Non Patent Literature 1), and performing a search using as a search key a short base sequence in a read sequence, and performing alignment in a region around (i.e., preceding and following) the matched region, taking into consideration possible sequencing errors and variations (see Non Patent Literature 2).

Typically, a next-generation DNA sequencer involves read errors of about 1%. Further, a very long genome region contains a number of similar sequences dispersed therein. Therefore, there is a possibility that a result of a mapping process performed on a per-read-sequence basis may contain errors. For example, there are cases where, although a given read sequence has no completely matching region in the reference genome sequence, it has a plurality of matching genome regions if it is supposed that there is a small number of sequencing errors. In such a case, which region is selected is at one's discretion, and the determination depends on the heuristic of the mapping process. Thus, in order to accurately analyze variations, a re-mapping process, which includes comparing mapping results of a number of read sequences and determining the majority, is performed in the following process, that is, in the downstream process (Non Patent Literature 3). Therefore, when the whole genome is analyzed, an amount of sequences that can cover several tens of times of the whole genome (which is greater than or equal to tens of giga bases) is determined. In addition, when a mapping destination is selected at one's discretion, it is concerned that a bias that depends on the mapping process may occur. Thus, results obtained by a plurality of mapping tools are compared with one another to check for the presence of such a bias. Patent Literature 1 is given as an example of patent literature related to such techniques.

CITATION LIST

Patent Literature

Patent Literature 1: JP 2003-330934 A

Non Patent Literature

Non Patent Literature 1: M. Burrows and D. Wheeler: A block-sorting lossless data compression algorithm. Technical Report 124, Digital Equipment Corporation, 1994.
Non Patent Literature 2: Li H. and Durbin R. (2009) Fast and accurate short read alignment with Burrows-Wheeler Transform. Bioinformatics, 25:1754-60.
Non Patent Literature 3: McKenna A, Hanna M, Banks E, Sivachenko A, Cibulskis K, Kernytsky A, Garimella K, Altshuler D, Gabriel S, Daly M, DePristo M A (2010). The Genome Analysis Toolkit: a MapReduce framework for analyzing next-generation DNA sequencing data. Genome Res. 20:1297-303.
Non Patent Literature 4: Mantaci, S., Restivo, A.; Sciortino, M: "An extension of the Burrows Wheeler transform to k words." Data Compression Conference, 2005. Proceedings. DCC 2005.
Non Patent Literature 5: Markus J. Bauer, Anthony J. Cox, Giovanna Rosone: "Light-weight BWT Construction for Very Large String Collections," Combinatorial Pattern Matching, Lecture Notes in Computer ScienceVolume 6661, 2011, pp 219-231
Non Patent Literature 6: Paolo Ferragina, Travis Gagie, Giovanni Manzini: "Light-weight Data Indexing and Compression in External Memory," Algorithmica, July 2012, Volume 63, Issue 3, pp 707-730.
Non Patent Literature 7: Kimura K, Suzuki Y, Sugano S, Koike A: "Computation of rank and select functions on hierarchical binary string and its application to genome mapping problems for short-read DNA sequences," J Comput Biol. 2009 November; 16(11):1601-13.
Non Patent Literature 8: Ge Nong; Sen Zhang; Wai Hong Chan; "Linear Suffix Array Construction by Almost Pure Induced-Sorting," Data Compression Conference, 2009. DCC '09., vol., no., pp. 193-202, 16-18 Mar. 2009

SUMMARY OF INVENTION

Technical Problem

As the aforementioned downstream process requires a huge computational cost to obtain high precision, it is impossible to handle all of read sequences obtained from a DNA sequencer at a time. Thus, for a gene region of interest, read sequences that are considered to be derived from the region with high possibility are selected using a result of a mapping process that adopts an efficient algorithm, and then, a downstream analysis is performed on the selected read sequences.

Meanwhile, there is known a method of identifying bacteria by creating a database of read sequence data, which has been obtained through a number of analyses performed using a capillary DNA sequencer with a relatively small number of (about 100) read sequences that are relatively long (i.e., a length of greater than or equal to 500 bases), conducting a search for homology using as a query a sequence of a gene region of interest in the genome, and making multiple alignments of the obtained read sequences (Patent Literature 1). However, the volume of data when the human genome is analyzed using a next-generation sequencer is as large as tens of giga bases or more. Thus, it is impossible to search for homology in a computation time that can withstand practical use.

When the whole genome of a human is analyzed, the total volume of read sequence data is as large as tens of giga bases. Thus, a mapping process requires a high computational cost even though an efficient algorithm is used. Thus, reducing the computational cost is an object to be achieved.

When a mapping destination is selected at one's discretion though it depends on the way in which a sequencing error is handled, selecting a mapping destination in a mapping process using heuristic means that a bias that depends on the mapping process is generated. Thus, providing a neutral processing method that can avoid such heuristic determination and can equally handle all of possible mapping destinations is an object to be achieved.

Currently, there exists only one type of reference genome sequence for a human except special regions, such as a human leukocyte antigen (HLA) region. However, if a plurality of types of reference genome sequences are prepared, it may become possible to analyze variations more precisely by selecting a reference genome sequence that is suitable for a race group to which a patient belongs from among the plurality of types of reference genome sequences. A mapping process is performed on a combination of all read sequences and a reference genome reference. Thus, changing the reference genome means starting all mapping processes from the beginning again. Thus, it is an object to be achieved to independently process all of read sequences and a reference genome sequence and thus suppress an increase in the computational cost when an analysis is performed by changing the combination.

It is object of the present invention to provide a data analysis device and a method therefor that can reduce a computational cost for a mapping process or can perform a neutral process by solving at least one of the aforementioned problems.

Solution to Problem

In order to achieve the aforementioned object, the present invention provides a data analysis device including a processing unit and a storage unit. The storage unit is configured to store a genome sequence database and a read sequence database, the genome sequence database having a collection of genome sequence data, and the read sequence database having a collection of read sequence data. The processing unit is configured to select a key sequence as a base sequence to be used for a search on the basis of a sequence of a specified genome region to be analyzed, determine a depth of the key sequence in the read sequence database, extract read sequence data containing the key sequence from the read sequence database, and compare the extracted read sequence data with the sequence of the genome region to analyze the data.

In addition, in order to achieve the aforementioned object, the present invention also provides a data analysis method performed by a processing unit of a data analysis device, including: using a genome sequence database and a read sequence database, the genome sequence database having a collection of genome sequence data in a form to allow retrieval of the genome sequence data, and the read sequence database having a collection of read sequence data in a form to allow retrieval of the read sequence data; selecting a key sequence as a base sequence to be used for a search on the basis of a sequence of a specified genome region to be analyzed; determining a depth of the key sequence in the read sequence database; and extracting read sequence data containing the key sequence from the read sequence database, and comparing the extracted read sequence data with the sequence of the genome region to analyze the data.

Advantageous Effects of Invention

According to an analysis device and a method therefor of the present invention, a computational cost can be suppressed. In addition, a neutral process can be performed without generation of a bias that depends on the processing method.

BRIEF DESCRIPTION OF DRAWINGS

FIG. 18 is a diagram showing Formulae 1 to 3 in accordance with a process of a data analysis method of an embodiment.

FIG. 19 is a diagram showing Formulae 4 to 7 in accordance with a process of a data analysis method of an embodiment.

DESCRIPTION OF EMBODIMENTS

Figure 1:
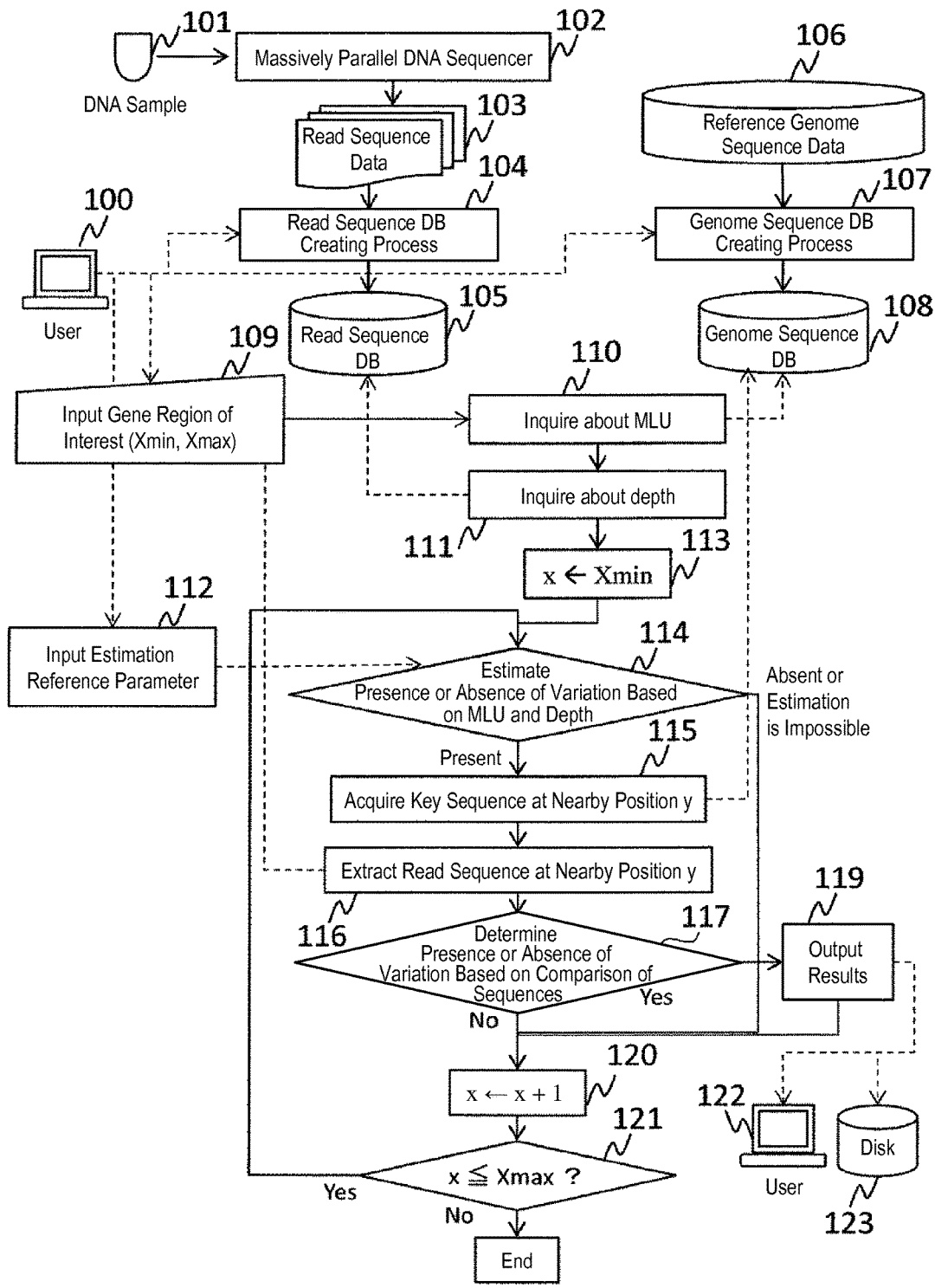
FIG. 1 is a flowchart showing the process produces for analyzing a variation in accordance with Embodiment 1.

Hereinafter, a variety of embodiments of the present invention will be described with reference to the drawings, but before that, a summary of a preferred configuration of the present invention will be described. According to a data analysis device and a method therefor of the present invention, a database is created by sorting all read sequences as well as cyclic permutations or suffixes thereof in the lexicographic order so as to allow a search to be performed using any short base sequence as a key and quickly return a result of the number of read sequences that contain the key sequence, and also allow quick extraction of all read sequences that contain the key sequence from among all read sequences.

On the reference genome sequence side, a database is created by inspecting in advance the length of bases at which a partial sequence starting from each base position of a reference genome sequence becomes unique in the reference genome sequence, taking a complementary strand into consideration, so as to be able to quickly return a result of the MLU (minimum length for uniqueness) that can ensue such uniqueness at any given base position. Such computation can be performed using the reference genome sequence data alone. Therefore, once such computation is performed on the reference genome sequence, the result can be reused for any read sequence data.

Further, in the downstream process of analyzing variations, the gene region of interest is scanned on a per-base basis, and the reference genome database is inquired of about the MLU at each base position, and further, a partial genome sequence with a length of the MLU is acquired by inquiring of the reference genome database. Then, the read sequence database is inquired of using the partial genome sequence with a length of the MLU as a search key so as to obtain the number (depth) of read sequences that contain the key sequence. If a base position at which the depth value is significantly lower than that in the neighboring region is found, such position is estimated to contain a variation with high possibility.

For a position that is estimated to contain a variation with high possibility, the reference genome database is inquired of again about the MLU at another position in the neighboring region where the depth is not low, and further, a genome base sequence with a length of the MLU is acquired by inquiring of the reference genome database. Then, the read sequence database is inquired of by using the genome base sequence with a length of the MLU as a search key so as to obtain all read sequences that contain the key sequence. Accordingly, read sequences that have a high possibility of being derived from the neighboring region can be collected. A detailed process of analyzing variations is performed on such read sequences.

Embodiment 1

Embodiment 1 is an embodiment of an analysis device that estimates, from a gene region of interest, a base position that has a high possibility of containing a variation on the basis of the MLU and the depth, and further determines the presence or absence of a variation at the estimated position on the basis of comparison of the sequences, and a method therefor.

FIG. 1 is a flowchart showing the process produces for analyzing a variation in accordance with this embodiment. It should be noted that an analysis device that realizes an analysis in accordance with each embodiment is implemented by a computer, such as a server with a configuration of a typical computer.

Figure 17:
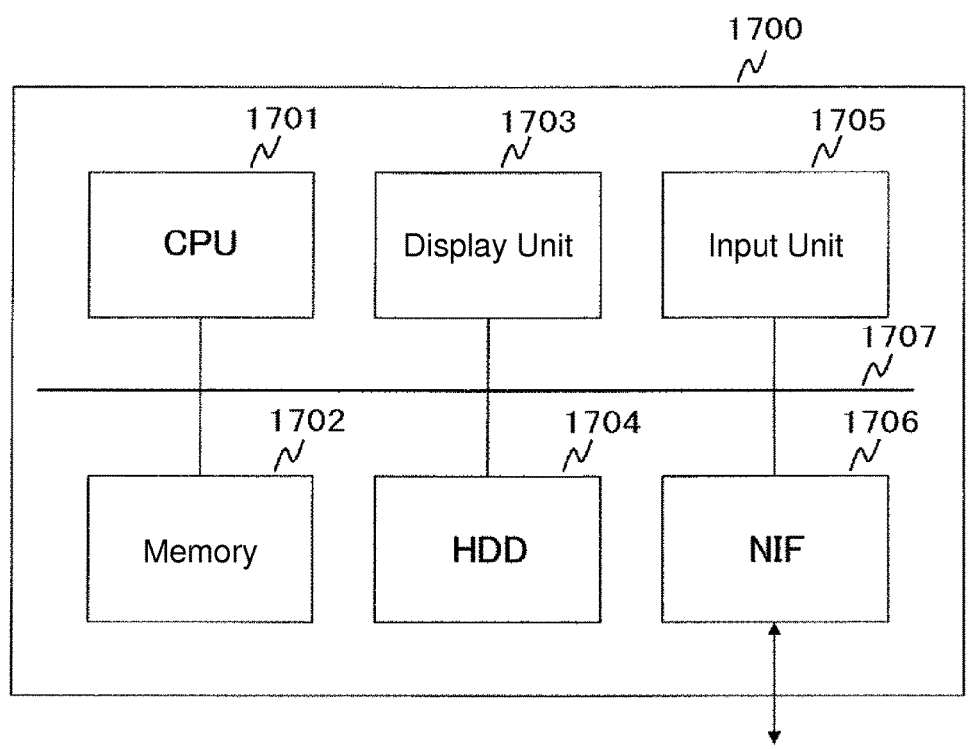
FIG. 17 is a block diagram showing an exemplary internal configuration of an analysis device in accordance with an embodiment.

FIG. 17 shows an exemplary configuration of an analysis device in accordance with all embodiments, inclusive of the present embodiment. In FIG. 17, an analysis device 1700 includes a CPU (Central Processing Unit) 1701 that is a processing unit, a memory 1702 that is a storage unit for storing programs and the like, a display unit 1703 for displaying a GUI (Graphical User Interface) for operations, analysis results and the like, a hard disk drive (HDD) 1704 functioning as a storage unit for storing databases (DBs), an input unit 1705, such as a keyboard, for receiving input parameters and the like, and a network interface (NIF) 1706 for connection to the Internet and the like, all of which are connected to a bus 1707. The databases (DBs) stored in the HDD 1704 can also be stored in a storage device that is provided outside the analysis device 1700, or can also be stored in a data center and the like via a network. A variety of flowcharts described in the following embodiment are implemented through execution of programs with the CPU 1701.

In the flowchart shown in FIG. 1, a DNA sample 101 is analyzed by a massively parallel DNA sequencer 102 to obtain read sequence data 103 composed of a number of short base sequences. A read sequence database (DB) creating process 104 is performed on such data to obtain a read sequence DB 105. In the read sequence DB creating process 104, all read sequences as well as cyclic permutations or suffixes thereof are sorted in the lexicographic order. When such a DB is created, it becomes possible to allow a search to be performed using any short base sequence as a key and quickly return a result of the number (depth) of read sequences that contain the key sequence, and also allow quick extraction of all read sequences that contain the key sequence from among all read sequences.

Reference genome sequence data 106 is subjected to a genome sequence DB creating process 107 to create a database, whereby a genome sequence DB 108 is constructed. The reference genome DB creating process includes inspecting the length of bases at which a partial sequence starting from each base position of a reference genome sequence becomes unique in the reference genome sequence, taking a complementary strand into consideration, and storing such information. Creating such a DB can quickly return a result of the minimum length for uniqueness (MLU) that can ensue such uniqueness at any given base position. In addition, the base sequences are stored as they are in the order of the coordinates so that the result of base sequences in any specified coordinate range can be quickly returned.

The MLU at the coordinate x, that is, the minimum length at which a partial sequence starting from x becomes unique in the genome sequence is represented by L(x). In addition, the depth of a read sequence when the partial genome sequence with a length of L(x) starting from the coordinate x is used as a key sequence is referred to as a depth at x and is represented by D(x). Hereinafter, a notation shown in Formula 1 of FIG. 18 is introduced. When the notation of Formula 1 of FIG. 18 is used, if a search (i.e., scan) is performed in the genome coordinate increasing direction (i.e., in the forward direction), the MLU and the depth can be computed as in Formula 2 of FIG. 18. Meanwhile, if a search (i.e., scan) is performed in the genome coordinate decreasing direction (i.e., in the backward direction), the MLU and the depth can be computed as in Formula 3 of FIG. 18.

In the flowchart of FIG. 1, coordinates (Xmin,Xmax) that define the range of a gene region of interest are input (109). The MLU, that is, the value of L(x) is obtained for each x in the range of Xmin to Xmax by inquiring of the genome sequence DB (110). In addition, the depth D(x) at each x is obtained by inquiring of the read sequence DB (111).

Then, a parameter that serves as a reference to estimate the presence or absence of a variation is input (112), and the following repeating process is started by setting x to Xmin at the left end of the region of interest (113). The presence or absence of a variation at x is estimated on the basis of the MLU and the depth (114). If it is estimated that there is no variation or estimation cannot be performed, the value of x is immediately updated to x+1 (120). Otherwise, another base position y that is close to x is selected on the basis of the depth, and a partial genome sequence with a length of L(y) starting from y is acquired by inquiring of the genome sequence DB (115). Using the sequence as a key sequence, all read sequences that contain the key sequence are obtained by inquiring of the read sequence DB (116). Such read sequences are compared with the reference genome sequence in detail to perform an analysis of a variation (117). If a variation is found, the result is output to a terminal (122) and a storage device (123) (119). After that, x is updated to x+1 (120). If x is not beyond the right end of the region, the process is repeated (121). Otherwise, the process is terminated.

Figure 2:
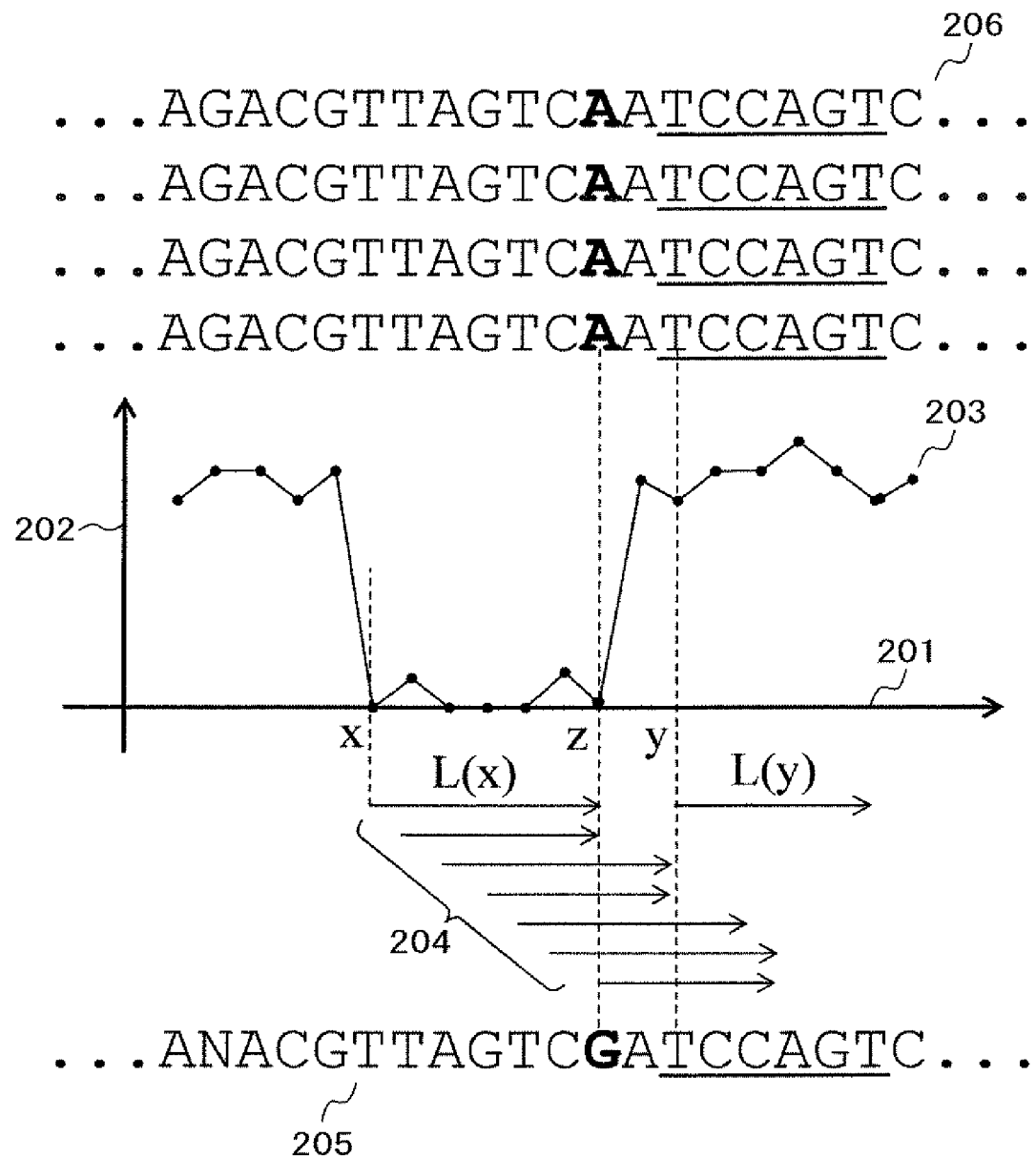
FIG. 2 is an illustration diagram for illustrating a method for determining the presence or absence of a variation through comparison of sequences in accordance with Embodiment 1.

FIG. 2 is an illustration diagram for illustrating a method for determining the presence or absence of a variation through comparison of sequences at the position x that has been estimated to contain a variation by performing a search in the forward direction in the analysis method of Embodiment 1 described above. The same is true of a case where a search is performed in the backward direction. A graph 203 in FIG. 2 is obtained by plotting the depth D(x) at the position coordinate x, where the abscissa 201 indicates the genome position coordinate and the ordinate 202 indicates the count number. Provided that a SNP is present at a genome position coordinate z, if a partial genome sequence, which has a length of L(x) starting from the position x, passes through z as shown in the range indicated by reference numeral 204, the value of the depth D(x) is significantly smaller than that in the neighboring region. The position at which the depth is small is, when a search is performed in the forward direction, on the backward direction side of the position at which a variation is present. Thus, any given position y at which the depth D(y) is not small is selected as the position y in the neighboring region on the forward direction side of the position x at which the depth decreases. A partial genome sequence with a length of L(y) starting from y is acquired by inquiring of the genome sequence DB. Then, using the sequence as a key sequence, all read sequences that contain the key sequence are collected by inquiring of the read sequence DB.

Reference numeral 206 represents the collected read sequences, and portions corresponding to the key sequence are indicated by underlines. Reference numeral 205 represents a genome sequence around x, and a portion corresponding to the key sequence is indicated by an underline. The genome sequence 205 around x can be obtained by inquiring of the genome sequence DB. The collected read sequences 206 are just some of vast amounts of all pieces of read sequence data. Thus, the computational cost for comparing such collected read sequences 206 with the genome sequence 205 around x can be suppressed. Such sequences are aligned with reference to the key sequence, and a search for a variation is performed in the neighboring region on the backward direction side of y. If a variation is found (in the example herein, there is a single base variation of from G to A as shown by bold characters at the position z), a variation is determined to be present. Otherwise, a variation is determined to be absent.

Figure 3:
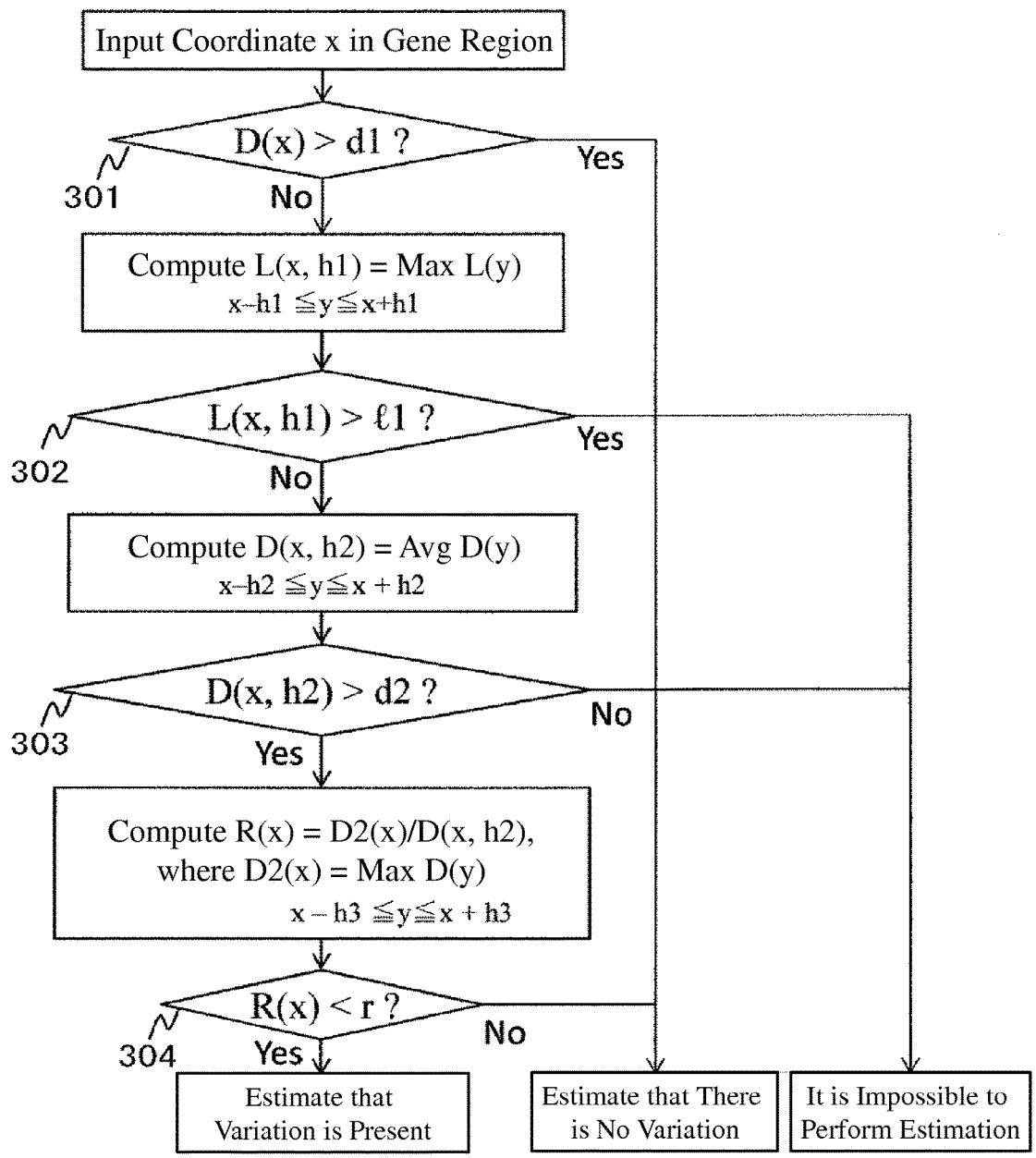
FIG. 3 is a flowchart showing a method for estimating the presence or absence of a variation on the basis of the MLU and the depth in accordance with Embodiment 1.

FIG. 3 is a flowchart showing a method for estimating the presence or absence of a variation at the base position x on the basis of the MLU and the depth in accordance with this embodiment. With respect to each base position y in the neighboring region of x, inclusive of x, it is assumed that the values of the MLU and the depth, that is, the values L(y) and D(y) have been acquired as a result of inquiring of the genome sequence DB and the read sequence DB. Symbols d1, d2, h1, h2, h3, and l1 are estimation reference parameters. Such values are input before starting the process (112). If the depth D(x) is sufficiently large at the position x, a variation is estimated to be absent (301). If the MLU is large in the neighboring region of x, it is estimated that estimation cannot be performed (302). If the average depth in the neighboring region of x is not sufficiently large, it is estimated that estimation cannot be performed (303). If the depth at x is significantly smaller than that in the neighboring region, a variation is estimated to be present. Otherwise, a variation is estimated to be absent (304).

Figure 4:
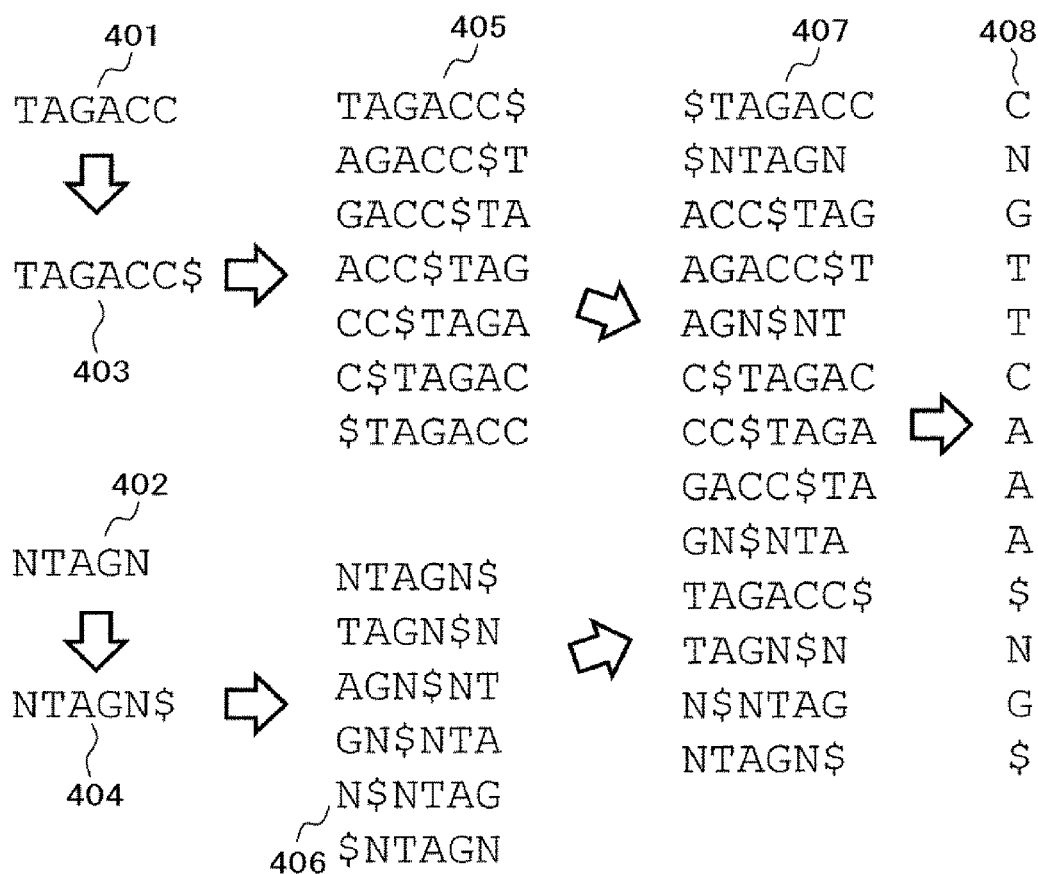
FIG. 4 is an illustration diagram that defines the generalized Burrows-Wheeler Transform (BWT) for data composed of a number of read sequences of unequal length in accordance with Embodiment 1.

FIG. 4 is an illustration diagram that defines the generalized Burrows-Wheeler Transform (BWT) for data composed of a number of read sequences of unequal length in this embodiment. The BWT is originally defined for a single character string (see Non Patent Literature 1 above), but the generalized BWT that is defined for a plurality of character strings is also known (see Non Patent Literature 4, Non Patent Literature 5, and Non Patent Literature 6 described at the end of the description of this embodiment). Herein, the BWT is generalized and defined for a number of read sequences of unequal length as described below. In FIG. 4, definitions for two read sequences are described for sake of simplicity. However, the BWT can be similarly defined even if the number of read sequences is increased.

It is assumed that reference numerals 401 and 402 in FIG. 4 are two target read sequences. Character strings obtained by adding the delimiter $ to the ends of the read sequences 401 and 402 are represented by reference numerals 403 and 404, respectively. Lists of character strings that are obtained by performing cyclic permutations (cyclic shift) on the entire character strings are represented by reference numerals 405 and 406. A list of character strings that is obtained by combining the two lists and sorting the sequences in the lexicographic order is represented by reference numeral 407. It should be noted that the order of comparison of alphabets is $<A<C<G<T<N$. Herein, the rank of N is put behind T because N is a special character that represents one of A, C, G, or T. While the two character strings are compared sequentially from the first characters, if the delimiter $ appears at the same character positions, the comparison process is not performed any further. Thus, the order of the following characters may be any order. A character string that is obtained by concatenating the last characters of the sorted character strings is represented by reference numeral 408. Herein, the character string 408 is shown vertically for ease of understanding of the correspondence. The character string 408 obtained by concatenating the last characters of the character string list (407), which has been obtained by sorting lists of character strings obtained by adding the delimiter $ to the ends of the read sequence data (401 and 402) and performing cyclic permutations thereon, in the lexicographic order is defined as the BWT of the read sequence data (401 and 402). In addition, reference numeral 407 obtained during the process is referred to as a SLCP (sorted list of cyclic permutations).

Figure 5:
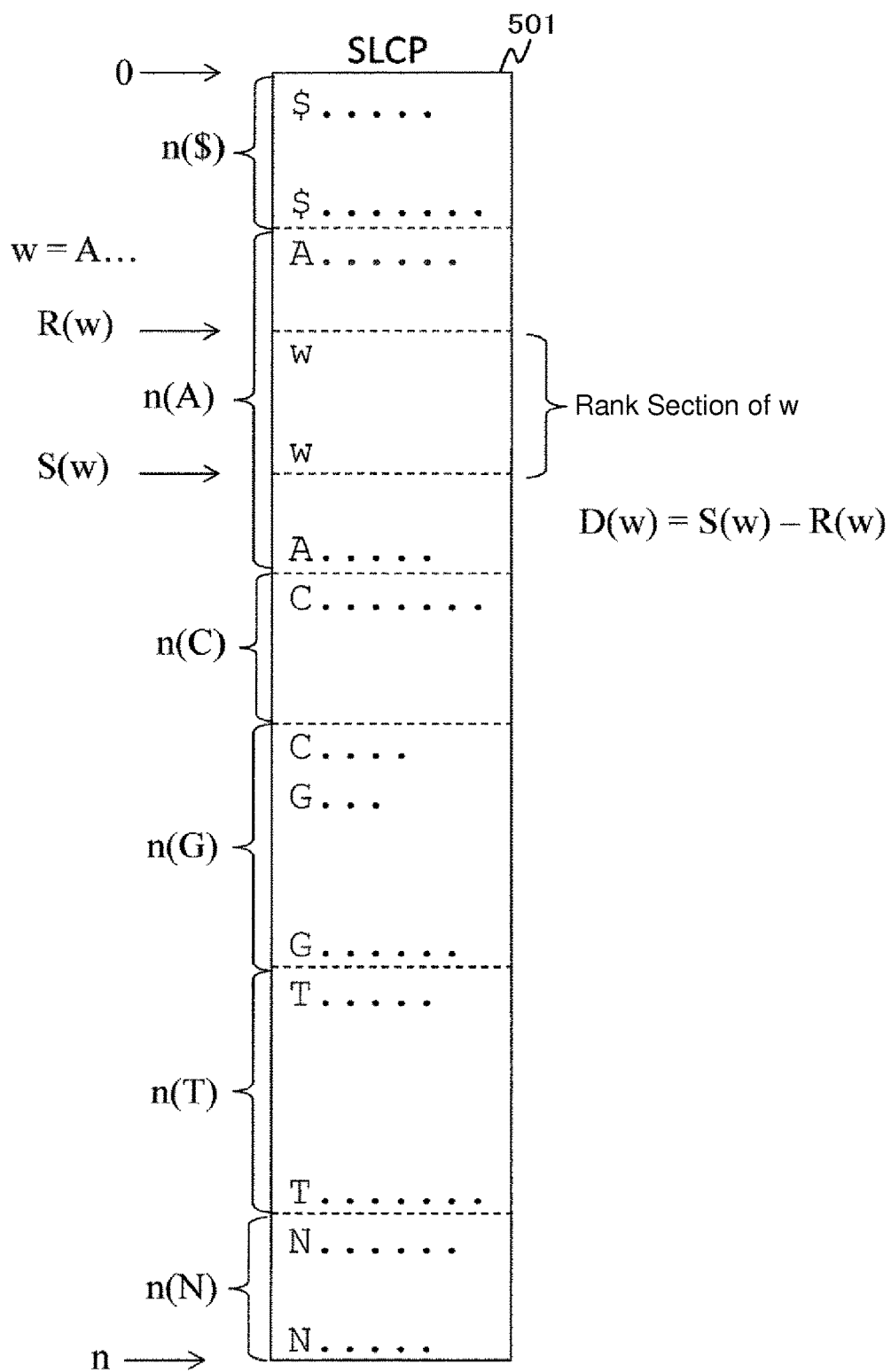
FIG. 5 is an illustration diagram showing a method for determining the depth D(w) of a character string w using a SLCP (sorted list of cyclic permutations) in accordance with Embodiment 1.

FIG. 5 is an illustration diagram showing a method for determining the depth D(w) of a character string w using a SLCP in this embodiment. Reference numeral 501 represents a SLCP. A character string obtained by concatenating the last character of each element in the SLCP 501 is the BWT, though the BWT is not shown in FIG. 5 to avoid complexity. As the SLCP has been sorted in the lexicographic order, a character string obtained by concatenating the head characters of the SLCP 501 is in the form shown in Formula 4 of FIG. 19.

As the SLCP has been sorted in the lexicographic order, if a given character string w composed of A, C, G, T, and N is compared with the elements of the SLCP sequentially from the first characters, it is possible to determine the position R(w), which is a position immediately before an element starting with w appears in the SLCP, and the position S(w), which is a position immediately after an element starting with w appears in the SLCP. Herein, the position immediately before the first element of the SLCP is represented by zero, while the position immediately after the last element of the SLCP is represented by the total number of elements n in the SLCP. The number n is equal to the sum of the total number of bases in the read sequence data and the number of read sequences, and is given by Formula 5 in FIG. 19.

If the SLCP contains even a single element starting with w, R(w)<S(w) is satisfied, and the difference S(w)−R(w) is equal to the number of times the character string w appears in the entire read sequence data, that is, the depth D(w) of w. Meanwhile, if the SLCP does not contain such an element at all, R(w)=S(w) is satisfied, which shows the insertion position for adding w to the SLCP without changing the lexicographic order. (R(w), S(w)) is referred to as a rank section of the character string w. It should be noted that during comparison of character strings, comparison of characters is performed sequentially from the first characters until when a different character appears or the delimiter $ appears for the first time. Thus, even when the last character of w is $, the rank section (R(w), S(w)) for w is determined.

Figure 6:
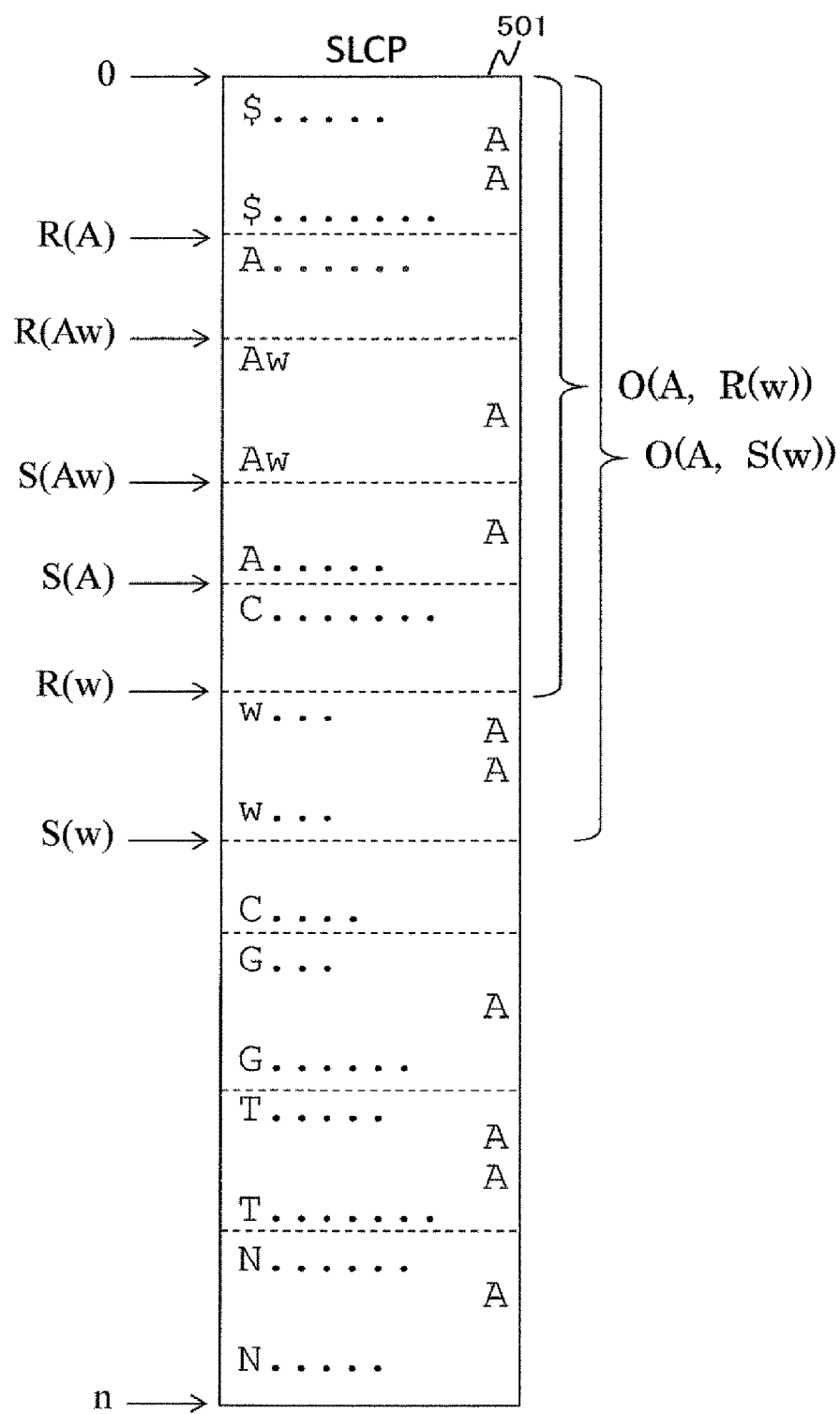
FIG. 6 is an illustration diagram illustrating an auxiliary function that is used when the BWT is used in accordance with Embodiment 1.

FIG. 6 is an illustration diagram illustrating an auxiliary function that is used when the BWT is used in this embodiment. The BWT is obtained by concatenating the last characters of the elements (i.e., character strings) of the SLCP (501). Although the lengths of such character strings typically differ from one another, FIG. 6 shows an example in which the last characters of such character strings are right-aligned, and the character A appears in places.

With respect to a given integer r in the range of zero to n and a character z of one of A, C, G, T, N, or $, the number of times the character z appears in the range of the first character to the r-th character in the character string BWT is represented by O(z, r). The number of times O(z, r) a specific character z appears in the range from the first position to the specified position r in the character string is referred to as a rank function, and a method for efficiently computing such a rank function is known (Non Patent Literature 7). It should be noted that when r=n, O(z, n)=n(z) is satisfied for each z=$, A, C, G, T, and N. Such values are already determined by scanning the entire read sequence data only once in advance.

The SLCP has been sorted in the lexicographic order. Thus, elements that are sequentially extracted from the SLCP are also sorted in the lexicographic order. In particular, with respect to a character z of one of A, C, G, T, N, or $, elements starting with z that are extracted from the SLCP, that is, elements in the range of R(z) to S(z) are sorted in the lexicographic order. Likewise, with respect to a character z of one of A, C, G, T, N, and $, elements ending with z that are extracted from the SLCP are also sorted in the lexicographic order. The SLCP is composed of all character strings generated through cyclic permutations (cyclic shift). Therefore, the entire element starting with z is made to correspond one-to-one with the entire element ending with z by cyclic permutations. In particular, with respect to a given character string w composed of A, C, G, T, and N, the entire character string starting with zw is made to correspond one-to-one with the entire character string starting with w and ending with z by cyclic permutations. The entire character string starting with zw is given by the rank section (R(zw), S(zw)) in the SLCP, while the entire character string starting with w and ending with z is given by the entire element ending with z in the rank section (R(w), S(w)) in the SLCP. Typically, these occupy discrete ranks in the rank section (R(w), S(w)) in the SLCP.

Figure 7:
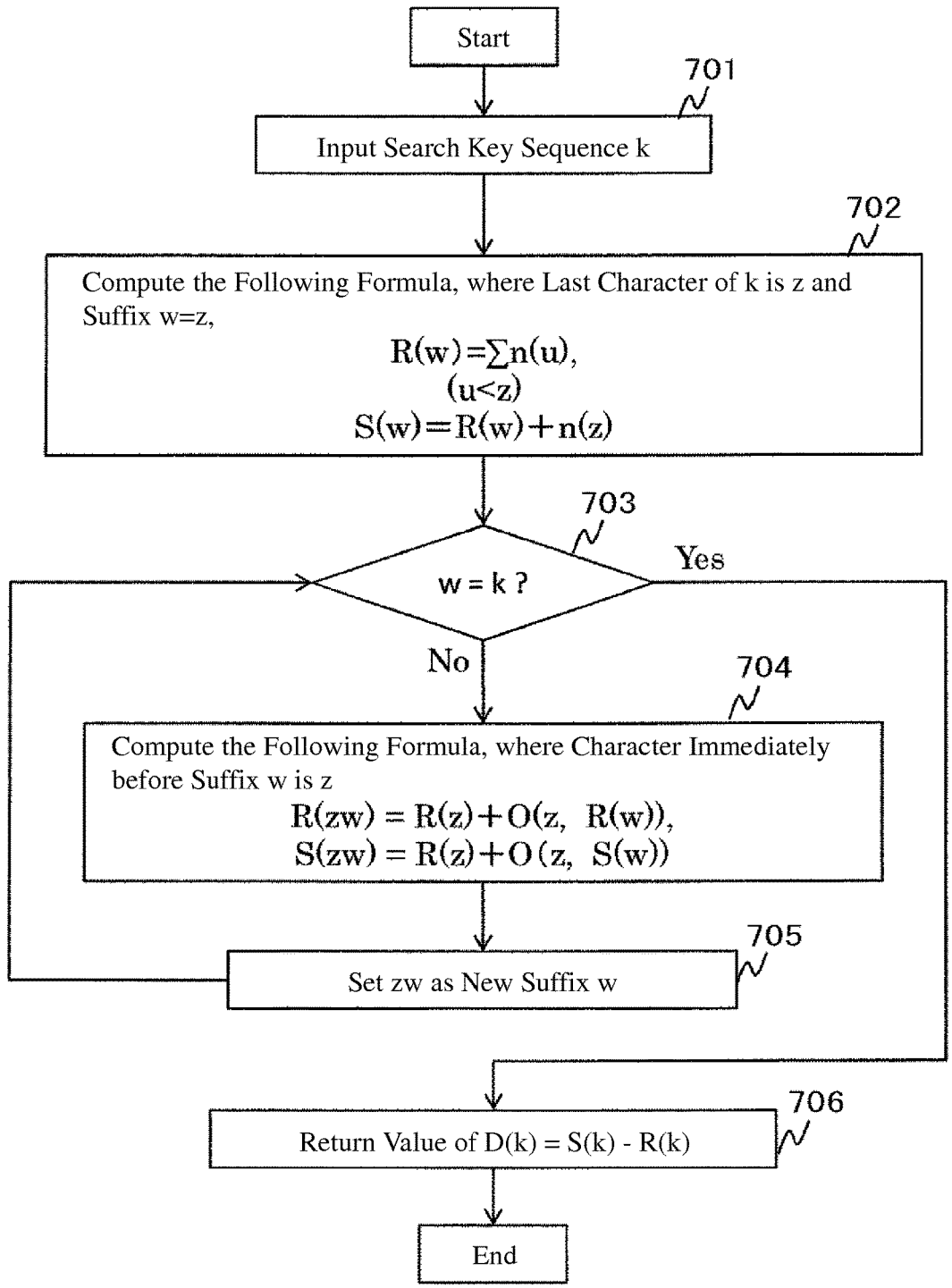
FIG. 7 is a flowchart for computing the depth for a search key sequence in accordance with Embodiment 1.

FIG. 7 is a flowchart showing a method for computing the depth for a search key sequence using the aforementioned one-to-one correspondence in this embodiment. A key sequence k is input (701), and w is set to a character string consisting of a single character z that is the last character of k (i.e., suffix of k of length one). The values of R(w) and S(w) for when w=z can be immediately computed because the value of n(u) for all characters u is already known (702). If the suffix w coincides with the key sequence k, the value of the depth D(k) is computed from the values of R(k) and S(k), and the process is terminated (706). Otherwise, the following process is repeated (703). In the key sequence k, provided that a character immediately before the suffix w is z, the values of R(zw) and S(zw) are computed using the aforementioned one-to-one correspondence (704). Herein, the value of R(z) can be computed as the sum of n(u) for characters u whose ranks are lower than the rank of z as in 702. Zw is set as a new w (705) and the process is repeated again from 703.

Figure 8:
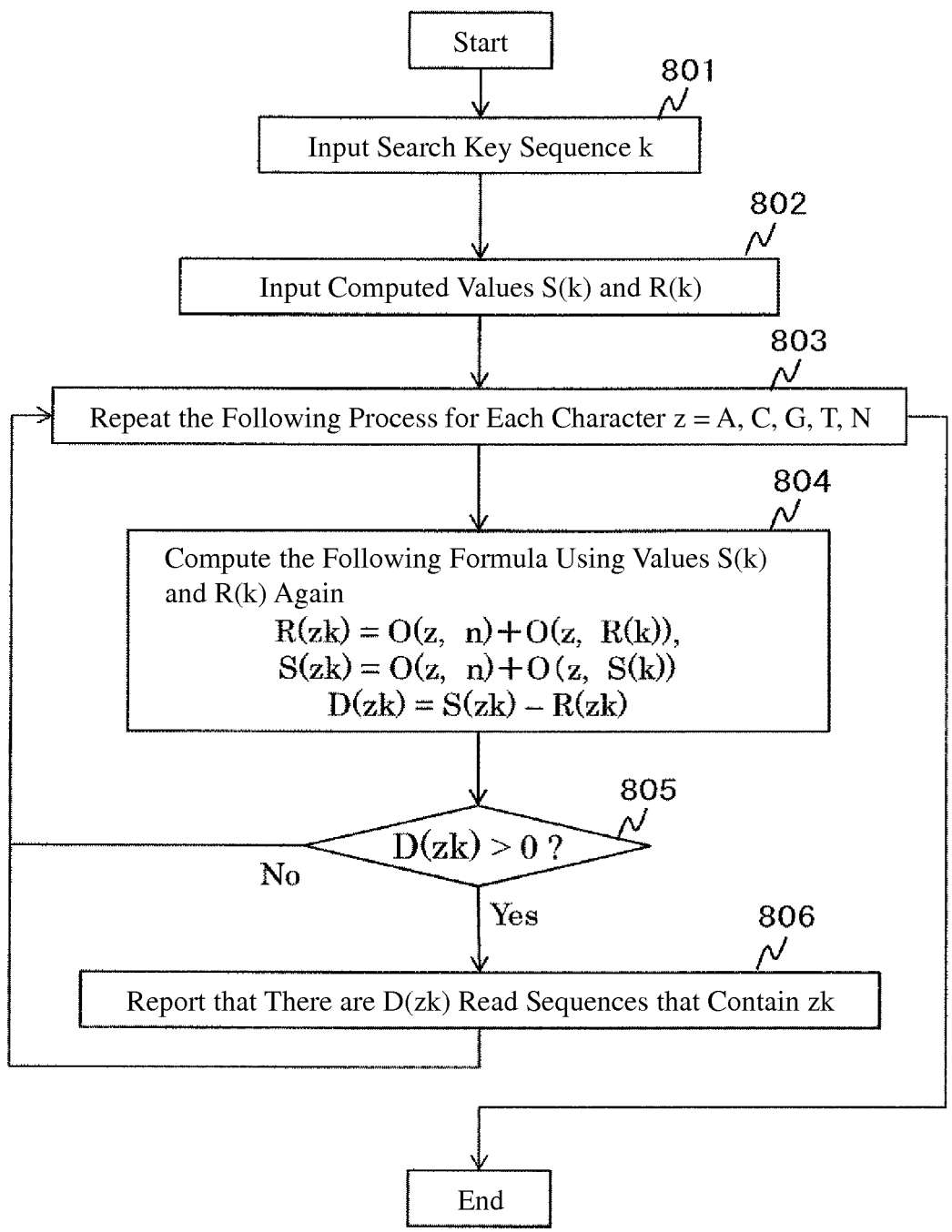
FIG. 8 is a flowchart showing a method for classifying all read sequences that contain a key sequence by a base located at the left of the key sequence, and determining the number of matching read sequences.

FIG. 8 is a flowchart showing a method for classifying all read sequences that contain a key sequence by a base located at the left of the key sequence, and determining the number of matching read sequences in this embodiment. It is assumed that the values S(k) and R(k) for the key sequence k have been computed using the aforementioned method.

The following process is repeated for each character z of A, C, G, T, N, and $ (803). The depth D(zk) for a character string zk can be computed using the aforementioned one-to-one correspondence of cyclic permutations (804). If the value is positive (805), it means that there are D(zk) sequences containing zk. Thus, a report is made (806).

FIG. 8 shows a method for extending a key sequence to the left side by one base using each base and determining the depth for the key sequence. By repeating such a method, it is possible to extend a key sequence to the left side by a plurality of bases using a variety of bases and compute the respective depths. In addition, if the extended sequences are overlapped with one another using the degree of overlap indicated by the respective values of the depth, it becomes possible to extract all of the read sequences that contain the original key sequence, which have been extended to the left side by a plurality of bases, inclusive of the degree of overlap, from the entire read sequence data.

Figure 9:
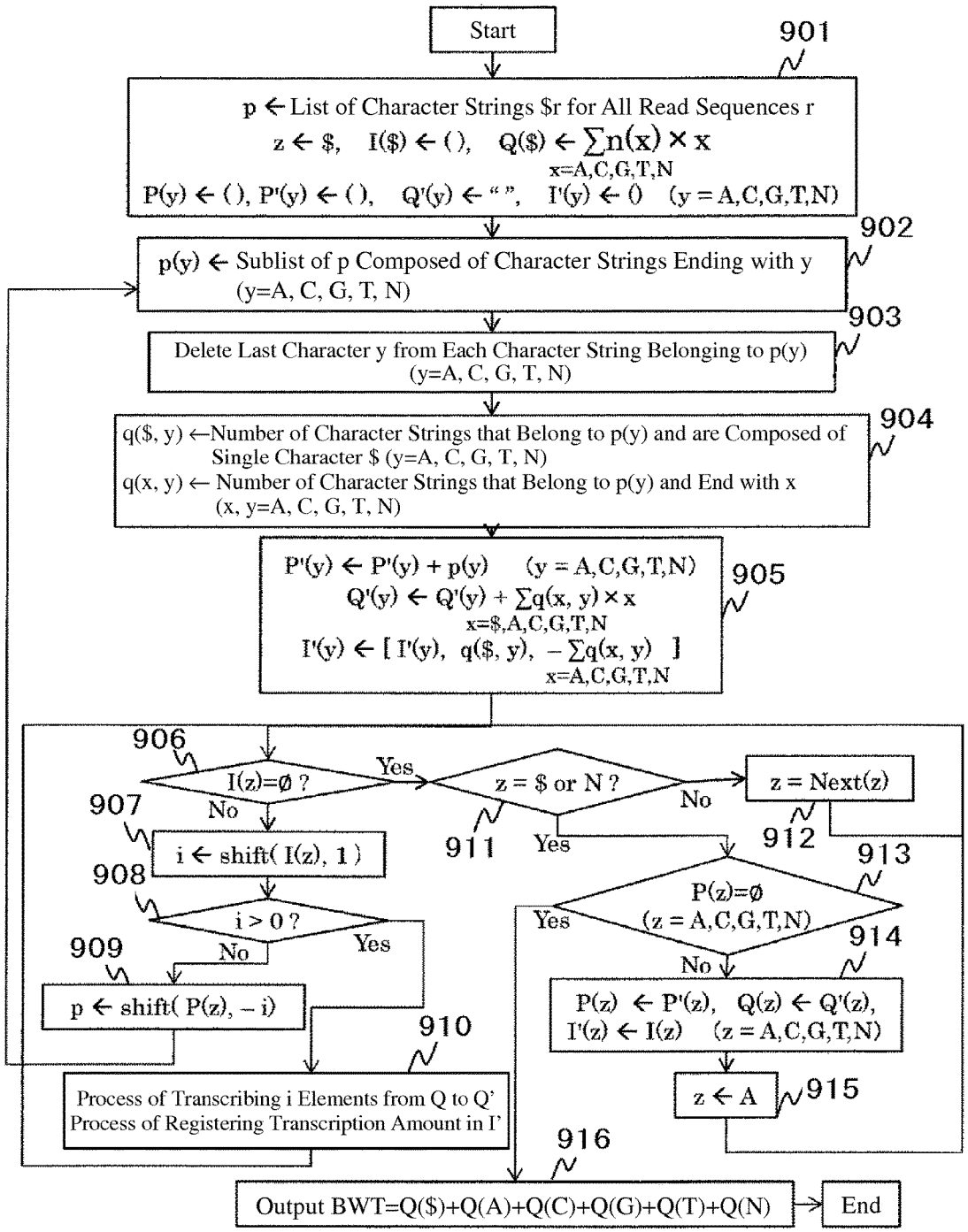
FIG. 9 is a flowchart showing a method for computing the BWT in accordance with Embodiment 1.

FIG. 9 is a flowchart showing a method for computing the BWT in this embodiment. The aforementioned one-to-one correspondence of cyclic permutations is also used for computing the BWT.

First, in 901, a process corresponding to a sublist composed of n($) elements starting with $ in the SLCP is performed. A character substring of the first n($) characters of the corresponding BWT is represented by Q($). Q($) contains all base characters A, C, G, T, N, which are contained in the read sequence data. If read sequence data contains empty read sequences, such sequences are removed in advance. Consequently, Q($) does not contain $. During comparison of character strings in the sorting process, characters that are behind $ are not compared. Thus, the arrangement order of such characters in Q($) may be any order. Herein, it is assumed that Q($) is a character string shown in Formula 6 of FIG. 19. Repeated characters are indicated by symbol ×, and concatenation of characters is represented by symbol + or Σ, whereby Q($) is computed in accordance with the formula indicated by reference numeral 901.

In addition, the delimiter $ is added to the heads of all read sequences r to create a list p in which the sequences are arranged in a given order. Symbol p represents a list composed of the elements in the SLCP that belong to the rank section of the character string $, and the last character of each element of p is registered in Q($) as a character substring of the BWT. In addition, z=$, I($) is set as an empty numerical value list, and for each of y=A, C, G, T, and N, P(y) and P'(y) are set as empty lists, Q'(y) is set as an empty character string, and I'(y) is initialized to an empty numerical value list, so that the process proceeds to a repeating process of from 902. ( ) represents an empty list, and " " represents an empty character string.

In 902, symbol p represents a list of character strings of from $ of the elements in the SLCP that belongs to the rank section of a given character string w$, and the last character of each element of p is already registered in one of Q(y) as a character substring of the BWT. However, the last characters of the elements in the SLCP, which have been made to have one-to-one correspondence so that the last characters appear as the first characters by performing cyclic permutations (hereinafter referred to as shifted elements), are not registered in any Q(y) yet.

Each element of the list p is classified by the last character. A sublist of p composed of elements ending with y is represented by p(y) for each of y=A, C, G, T, and N (902).

Next, the last character y is removed from the character string of each element of p(y) for each of y=A, C, G, T, N. This is a list of character strings of from $ of the shifted elements.

For each of y=A, C, G, T, N, the number of elements of p(y) that are composed of a single character $ is represented by q($,y), and the number of elements of p(y) other than those is counted by being classified by the last character x=A, C, G, T, and N. The counted number is represented by q(x,y) (904).

In 905, for each of y=A, C, G, T, and N, the last characters of the elements of the list p(y) determined in 903 are registered as a character substring of the BWT, at a position behind the character string Q'(z). During comparison of character strings in the sorting process, characters that are behind $ are not compared. Thus, the arrangement order of such characters in the character strings may be any order. Herein, a new character string that is obtained by concatenating the character strings in the form shown in Formula 7 of FIG. 19 is represented by Q'(z) (in the formula indicated by reference numeral 905, repeated characters are indicated by symbol × and concatenation of characters is represented by symbol + or Σ).

Among them, regarding the first q($,y) elements (which have $ at the end), the last characters of the shifted elements are already registered in Q($) in 901. Meanwhile, regarding the remaining q(A,y)+q(C,y)+q(G,y)+q(T,y)+q(N,y) . . . (Formula 8) elements (which have one of the characters of A, C, G, T, or N at the ends), the last characters of the shifted elements are not registered in any Q(y) yet. Herein, a list that is obtained by concatenating the list p(y) to a position behind the list P'(y) for each of y=A, C, G, T, and N for the following process is represented by a new list P'(y) (it should be noted that the concatenation of the lists is represented by symbol + in the formula indicated by reference numeral 905 of FIG. 9).

In addition, two elements: q($,y) and—(q(A,y)+q(C,y)+q(G,y)+q(T,y)+q(N,y)) . . . (Formula 9) are added at a position behind the numerical value list I'(y). Herein, a positive number represents the number of elements that have been registered, while a negative number represents the number obtained by inverting the sign of the number of elements that should be registered in the following process.

Next, whether the numerical value list I(z) is empty or not is inspected (906).

If the numerical value list I(z) is not empty, the first elements of the list are extracted and deleted, and the extracted elements are represented by i. If i is negative, the first (−i) elements are extracted and deleted from the character string list P(z), and a list composed of the extracted elements is represented by a new list p. As described in 905, the list p satisfies the conditions supposed in 902. Herein, the process is repeated again from 902. Meanwhile, if i is positive, the last characters of the elements obtained by shifting the next i elements of Q(z) are already registered in one of Q(y). Thus, such characters are transcribed to the new Q'(y), and the amount of transcription is registered in each I'(y) (910).

If the numerical value list I(z) becomes empty in 906, whether z is equal to $ or N is inspected (911). If z is not equal to either $ or N, z is replaced by a character Next(z) of the next rank (912), and the process is continued returning back to 906 again. Herein, Next(A)=C, Next(C)=G, Next(G)=T, and Next(T)=N   (Formula 10)

If z is equal to $ or N in 911, whether P(z) is an empty list or not is inspected for all of z=A, C, G, T, and N (913). If there is no empty list among them, P'(z), Q'(z), and I'(z) are set as new P(z), Q(z), I(z) for all of z=A, C, G, T, and N (914), and z is set as a character A of the first rank (915), and then, the process is repeated from 906 again.

In 913, if P(z) becomes an empty list for all of z=A, C, G, T, and N, the BWT is obtained by concatenating the character strings Q($), Q(A), Q(C), Q(G), Q(T), and Q(N), and then, the BWT is output (916).

Figure 10:
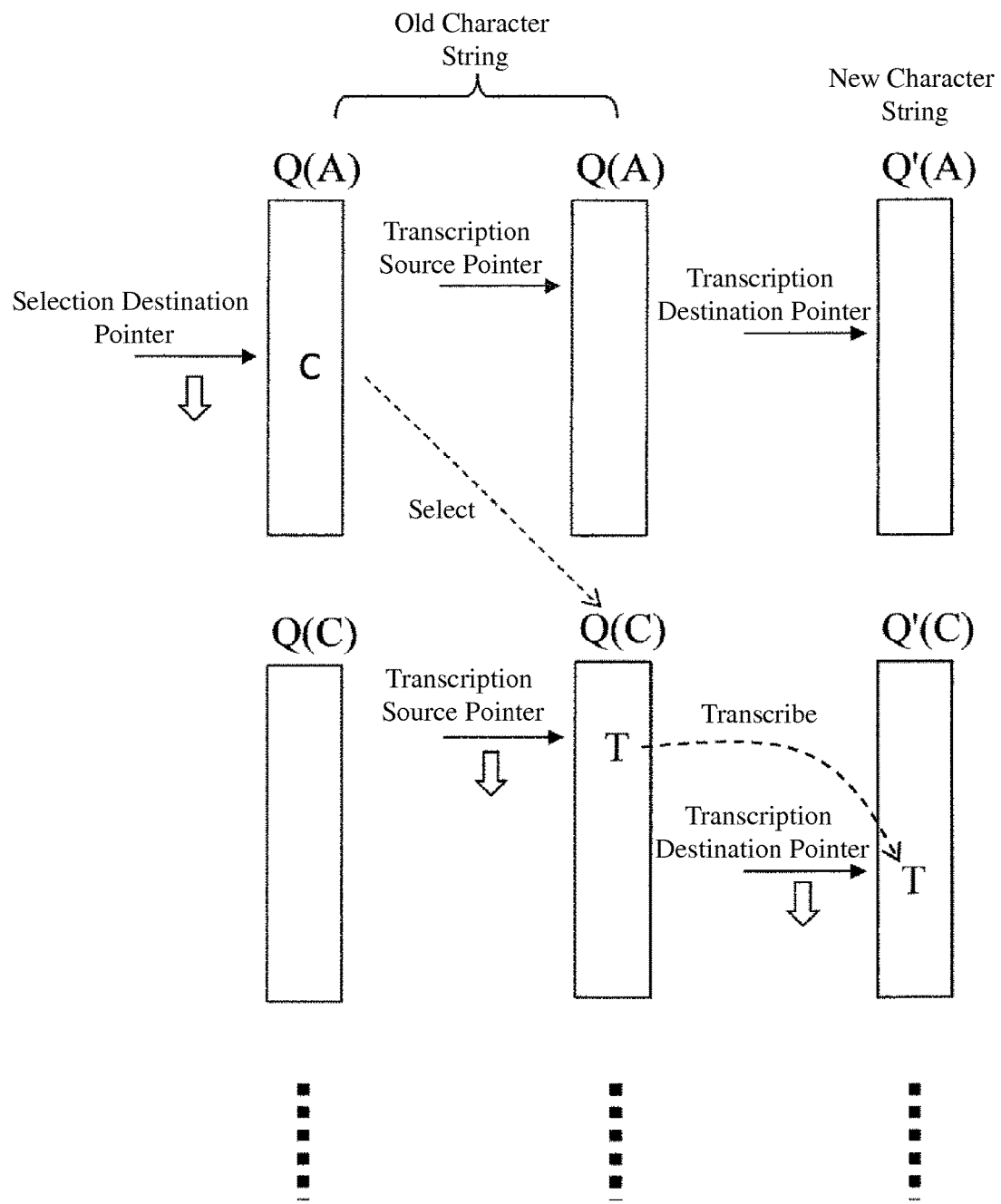
FIG. 10 is an illustration diagram showing a method for transcribing elements from an old character string to a new character string in accordance with Embodiment 1.

FIG. 10 is an illustration diagram showing a method for transcribing elements from an old character string Q to a new character string Q' in 910 of FIG. 9. There are a transcription source pointer that indicates the position of the transcription source in Q(z), and a transcription destination pointer that indicates the position of the transcription destination in Q'(z) for each of z=A, C, G, T, and N. The pointers are all initialized to zero when a process is started, are repeatedly updated in 910, and are all reset to zero in 914. There is also a selection destination pointer that selects a transcription target. The selection destination pointer indicates a position in Q(A), Q(C), Q(G), Q(T), and Q(N). The selection destination pointer is reset to the head of Q(A) when a process is started, is repeatedly updated in 910, is reset to the head of Q(z) for new z in 912, and is reset to the head of Q(A) in 915. For the old character string Q, two types of pointers that are the selection destination pointer and the transcription source pointer are used. Therefore, FIG. 10 repeatedly displays Q indicated by the selection destination pointer and Q indicated by the transcription source pointer to avoid confusion. However, the Q indicates an identical object.

In order to transcribe a single element from Q to Q' in 910, the following process is performed. First, a character y in the character string Q(z) indicated by the selection destination pointer is read, and the selection destination pointer is advanced by +1. In the example shown in FIG. 10, z=A and y=C. Q(y) is selected, and a character (T in the example shown in FIG. 10) indicated by the transcription source pointer is transcribed to the position indicated by the transcription destination pointer in Q'(y). Then, both the transcription source pointer and the transcription destination pointer are advanced by +1. In order to transcribe i elements from Q to Q' in 910, transcription of a single element is repeated i times. Consequently, after the transcription destination pointer in Q'(y) is advanced by +i(y) for each of y=A, C, G, T, and N, i(y) is added to the end of the numerical value list I'(y).

Figure 11:
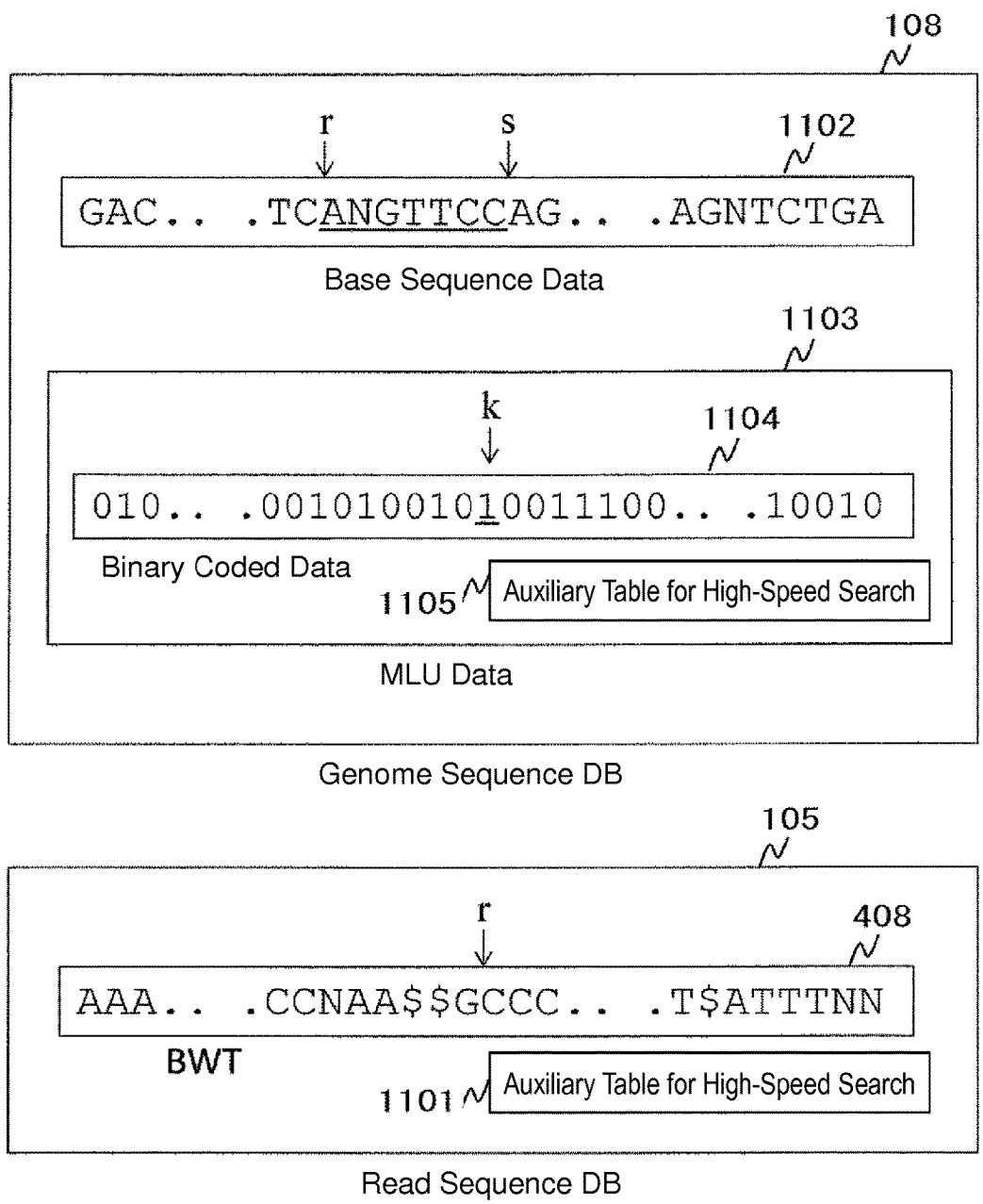
FIG. 11 is an illustration diagram showing the configurations of a genome sequence DB and a read sequence DB in accordance with Embodiment 1.

FIG. 11 is an illustration diagram showing the configurations of the genome sequence DB and the read sequence DB. The read sequence DB (105) includes the BWT (408) of the read sequence (106), and an auxiliary table (1101) that is necessary for high-speed computation of a rank function on the BWT. The genome sequence DB (108) includes base sequence data (1102) of the genome arranged in the order of the coordinates and MLU data (1103). A base sequence in any specified range can be quickly extracted from the base sequence data (1102). The MLU data includes binary coded data (1104) and an auxiliary table for search (1105).

The binary coded data (1104) of the MLU is a binary character string with a length of 2n, and is configured as follows. First, all elements are initialized to zero. The value L(x) of the MLU is computed for all base positions x in the reference genome sequence. Then, assuming that k(x)=2x+L(x)−1 . . . (Formula 11), the k(x)-th element of the binary coded data is set to 1. It should be noted that the first element is counted as the 0th element.

If a given genome coordinate x other than the end position has an integer l=L(x)−1, a sequence, which is equal to a sequence with a length of l starting from x, is located at a position y that is different from x, from the definition of the MLU at x. At this time, if the first character is ignored, it follows that a sequence, which is equal to a sequence with a length of (l−1) starting from x+1, is located at a position y+1 that is different from x+1. Thus, L(x+1) should be at least greater than (l−1) from the definition of the MLU at x+1.

Thus, $$l-1 < L(x+1) \therefore L(x)-l=1 L(x+1) \quad \text{(Formula 12)}$$

Consequently, $$k(x)=2x+L(x)-1 \le 2x+L(x+1) < 2x+1+L(x+1)=k(x+1) \quad \text{(Formula 13)}$$

That is, k(x) has a different value at each base position x, and this indicates a different element in the binary coded data. In addition, it is obvious that x<y implies k(x)<k(y). Thus, if binary coded data is obtained, it is possible to determine the value of L(x) at any genome coordinate x. That is, the position k(x) at which the x-th 1 appears in the binary coded data may be determined, and L(x) may be computed as follows.

$$L(x)=k(x)-2x+1 \quad \text{(Formula 14)}$$

The function k(x)=select(x) for determining the position at which the x-th 1 appears in the binary coded data is referred to as a select function, and a method for efficiently computing such function using an auxiliary table is known (Non Patent Literature 7). Reference numeral 1105 represents an auxiliary table used for computing a select function on the binary coded data (1104) at a high speed.

Figure 12:
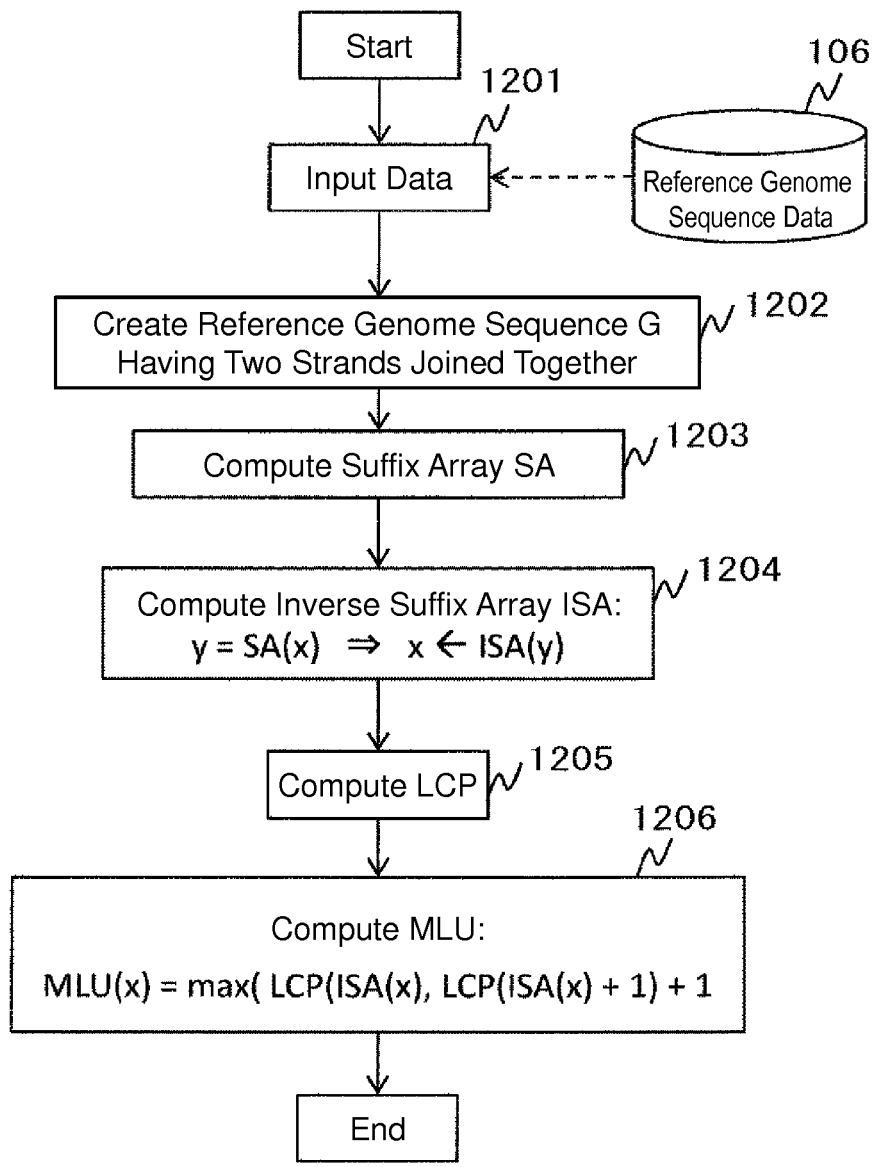
FIG. 12 is a flowchart showing a method for computing the value L(x) of the MLU at the genome coordinate x in accordance with Embodiment 1.

FIG. 12 is a flowchart showing a method for computing the value L(x) of the MLU at the genome coordinate x in the analysis method of this embodiment. The reference genome sequence data (106) is input (1201) to create a reference genome sequence G having two strands joined together (1202), and then, a suffix array SA of G is computed (1203). Symbol SA represents an integer array that is obtained by, when all suffixes of G are sorted in the lexicographic order, arranging integers indicating the start positions of the suffixes in the sorted order. In the case of the human genome, the genome size is about 3 giga bases. Thus, the length of G is about 6 giga. For G with such a size, SA can be efficiently computed using a known method (Non Patent Literature 8). The SA is a correspondence table for converting the sorted order of suffixes into start positions. Herein, an ISA (inverse suffix array) that is a correspondence table of inverse conversion of the SA is created (1204).

In addition, a LCP (longest common prefix length array) of G is computed (1205). If the r-th element for when the suffixes of G are sorted in the lexicographic order is represented by s(r), LCP is an integer array, and the r-th element of the LCP is defined as the length of the longest prefix that is common to s(r) and s(r−1). The LCP can be efficiently computed using a known method (reference-LCP). When s(r) and the element s(r−1) immediately before s(r) are compared sequentially from the first characters, they differ at the (LCP(r)+1)-th character. Likewise, when s(r) and an element s(r+1) immediately after s(r) are compared sequentially from the first characters, they differ at the (LCP(r+1)+1)-th character. Thus, the prefix of s(r) that has a length given by Formula 15 below is unique in the genome sequence G.

$$\max(\text{LCP}(r)+1, \text{LCP}(r+1)+1) \quad \text{(Formula 15)}$$

Herein, symbol max means the maximum value. Thus, the MLU (minimum length for uniqueness) that can ensure uniqueness can be computed using the formula indicated by reference numeral 1206.

As the DNA sample in this embodiment, a sample for whole-genome analysis, a sample for exome analysis, a sample obtained by capturing a DNA fragment of a target region of interest, or the like can be used.

Embodiment 2

As Embodiment 2, a position at which the possibility of splicing having occurred is high is estimated from a gene region of interest on the basis of the MLU and the depth. Further, an embodiment of an analysis device that determines the presence or absence of splicing at the estimated position on the basis of comparison of sequences, and a method therefor will be described.

Figure 13:
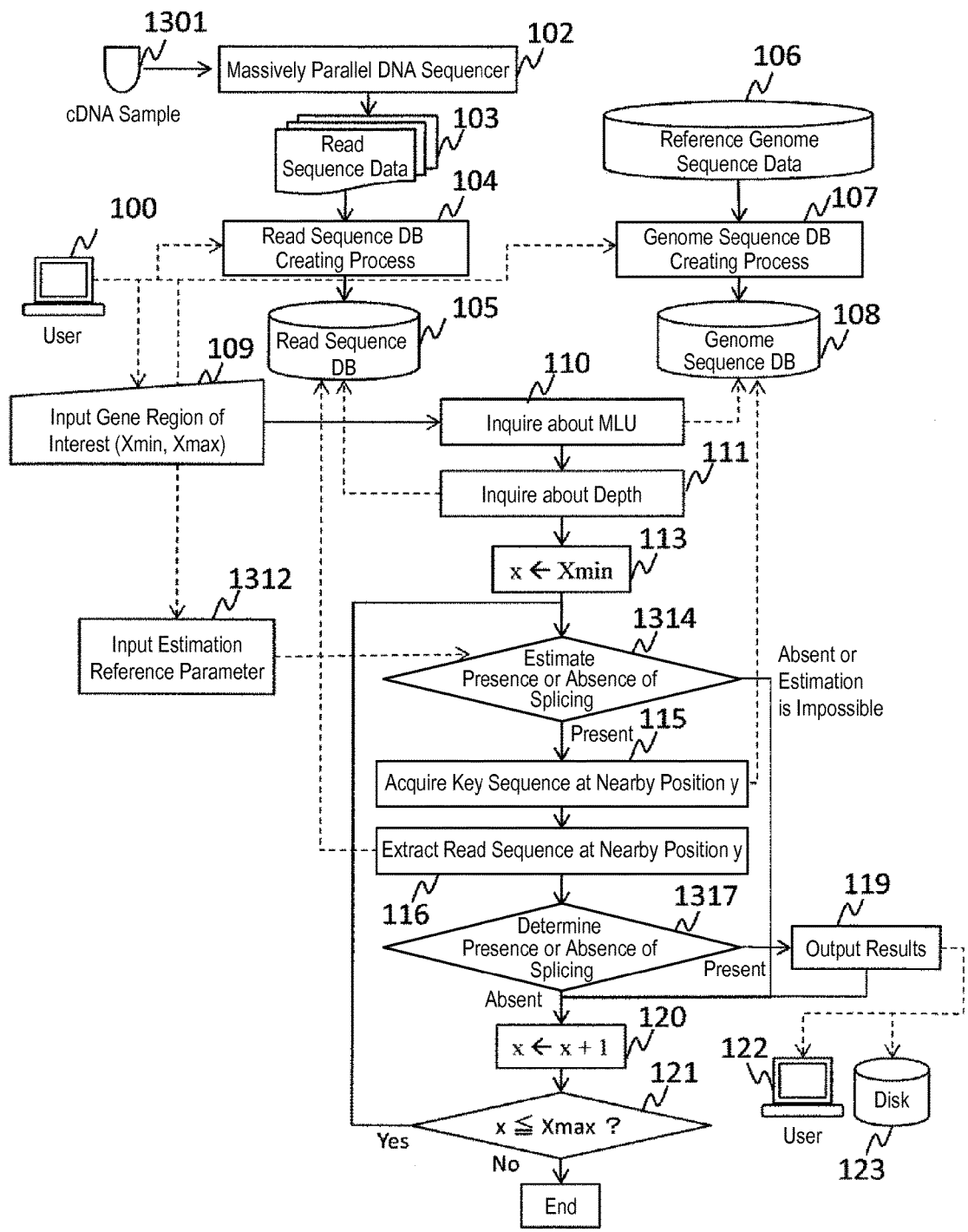
FIG. 13 is an illustration diagram showing a method for estimating the position where the possibility of splicing having occurred is high from a gene region of interest on the basis of the MLU and the depth, and further determining the presence or absence of splicing at the estimated position on the basis of comparison of sequences in accordance with Embodiment 2.

FIG. 13 is a flowchart showing the process procedures for analyzing splicing of the transcriptome in Embodiment 2.

A cDNA sample (1301) is analyzed by the massively parallel DNA sequencer (102) to obtain read sequence data (103) composed of a number of short base sequences. Then, the read sequence DB creating process (104) is performed as in Embodiment 1 to obtain the read sequence DB (105).

The reference genome sequence data (106) is also subjected to the genome sequence DB creating process (107) to create a database as in Embodiment 1, whereby the genome sequence DB (108) is constructed.

Coordinates (Xmin,Xmax) that define the range of a gene region of interest are input (109). The MLU, that is, the value of L(x) is obtained for each x in the range of Xmin to Xmax by inquiring of the genome sequence DB as in Embodiment 1 (110). In addition, the depth D(x) at each x is obtained by inquiring of the read sequence DB (111).

A parameter that serves as a reference for estimating the presence or absence of splicing is input (1312), and the following repeating process is started by setting x to Xmin at the left end of the region of interest (113). The presence or absence of splicing at x is estimated on the basis of the MLU and the depth (1314). If it is estimated that there is no splicing or estimation cannot be performed, the value of x is immediately updated to x+1 (120). Otherwise, another base position y that is close to x is selected on the basis of the depth, and a partial genome sequence with a length of L(y) starting from y is acquired by inquiring of the genome sequence DB (115). Using the sequence as a key sequence, all read sequences that contain the key sequence are obtained by inquiring of the read sequence DB (116). Such read sequences are compared with the reference genome sequence in detail to determine the presence or absence of splicing (1317). If a splicing is determined to be present, the result is output to the terminal (122) and the storage device (123) (119). After that, x is updated to x+1 (120). If x is not beyond the right end of the region, the process is repeated (121). Otherwise, the process is terminated.

Figure 14:
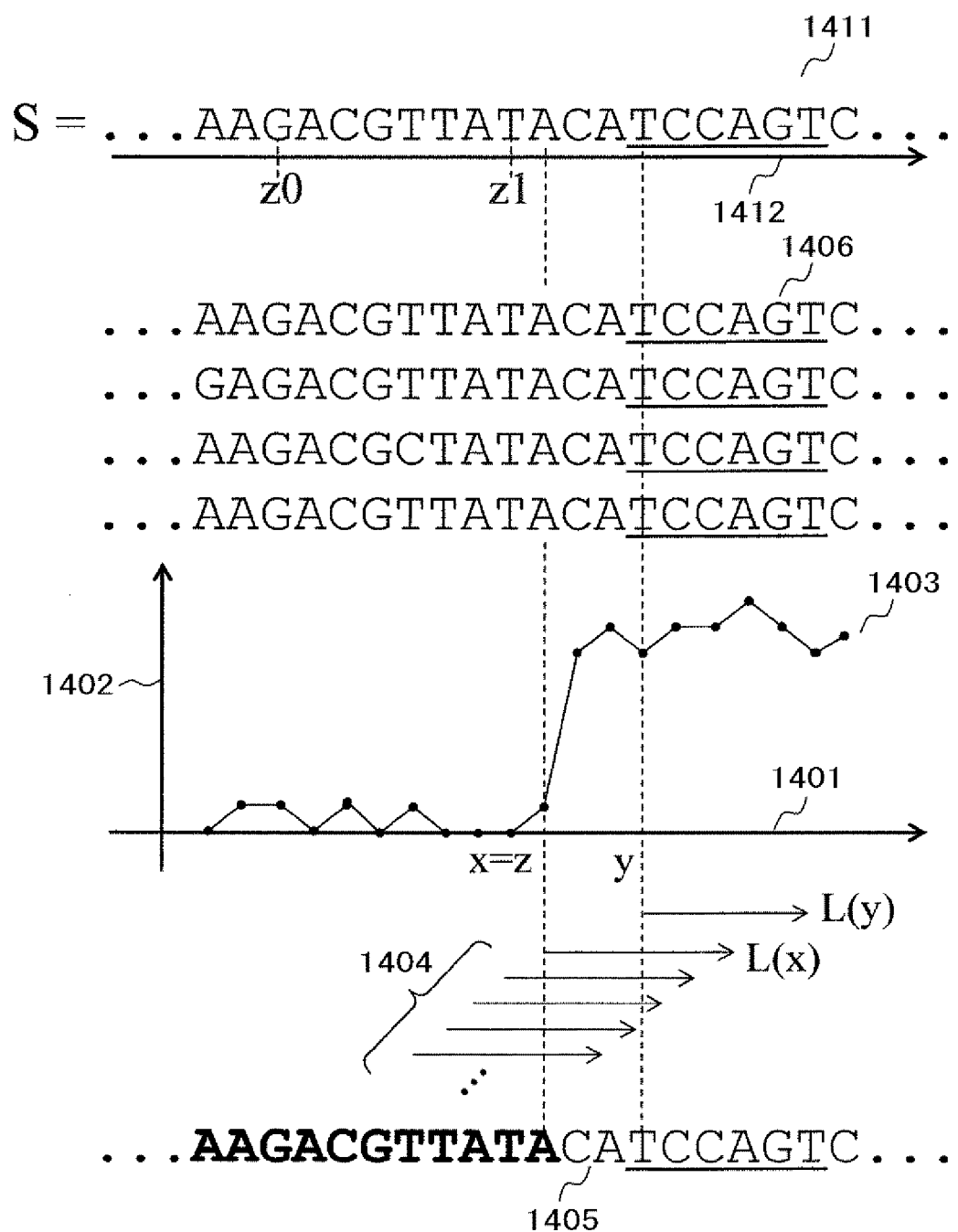
FIG. 14 is an illustration diagram for illustrating a process of determining the presence or absence of splicing through comparison of sequences at a position that has been estimated to contain splicing by performing a search in the forward direction in accordance with Embodiment 2.

FIG. 14 is an illustration diagram for illustrating a process of determining the presence or absence of splicing through comparison of sequences at a position x that has been estimated to contain splicing by performing a search in the forward direction (i.e., in the genome coordinate increasing direction) in this embodiment. The same is true of a case where a search is performed in the backward direction. The abscissa 1401 indicates the genome position coordinate, and the ordinate 1402 indicates the count number, and a graph 1403 is obtained by plotting the depth D(x) at the position coordinate x. Suppose that the genome coordinate is at a position z, and splicing is generated such that an intron is located on the backward direction side of the genome coordinate (i.e., in the genome coordinate decreasing direction) with its end located at the position z, and an exon is located on the forward direction side thereof. As shown in the range indicated by reference numeral 1404, if a partial genome sequence with a length of L(x) starting from the position x is contained in the intron or passes through z, the value of the depth D(x) is significantly smaller than that in the neighboring region on the forward direction side of z. That is, on the backward direction side of z, the depth is significantly smaller than that on the forward direction side of z.

Herein, with respect to a position coordinate x that is the boundary between which the depth becomes significantly smaller in the backward direction side than that on the forward direction side, a given position y at which the depth is not small is selected in the neighboring region on the forward direction side of x. A partial genome sequence with a length of L(y) starting from y is acquired by inquiring of the genome sequence DB. Then, using the sequence as a key sequence, all read sequences that contain the key sequence are collected by inquiring of the read sequence DB. Reference numeral 1405 represents a genome sequence around x, and a portion corresponding to the key sequence is indicated by an underline. Reference numeral 1406 represents the collected read sequences, and portions corresponding to the key sequence are indicated by underlines. A genome sequence 1405 around x can be obtained by inquiring of the genome sequence DB.

The collected read sequences 1406 are just some of all pieces of a large volume of read sequence data. Thus, a computation cost for the following process can be suppressed. Reference numeral 1411 represents a common sequence S of the read sequences. This is obtained by aligning the read sequences that belong to reference numeral 1406 at the position of the key sequence and arranging the bases that appear most frequently at the respective base positions. On the common sequence S, a coordinate system (1412), which is obtained by extending the base position coordinate of the corresponding genome sequence G at the key sequence (i.e., underlined portion), is used. The common sequence S is analyzed, and if splicing is detected, the detected splicing is reported.

Herein, the notation and terminology shown in Formula 16 below are introduced to represent the character substring of the common sequence S and the depths in the genome sequence data and the read sequence data.

$S[z0, z1]$: A partial sequence of S whose position coordinate is greater than or equal to z0 and less than or equal to z1.

$Occ(s, G)$: The number of times the base sequence s appears as a partial sequence of G (the number of appearances)

(the depth of s in the genome sequence data)

$Occ(s, R)$: The number of times the base sequence s appears as a partial sequence of R (the number of appearances)

(the depth of s in the read sequence data)

$Loc(s, G)$: The appearance position coordinate at which the base sequence s uniquely appears as a partial sequence of G (when $Occ(s, G)=1$) - - - (Formula 16)

Herein, the depth of s in the read sequence data can be computed more efficiently using the method described with reference to FIG. 7 in Embodiment 1. The depth of s in the genome sequence data can be similarly computed using the BWT of the reference genome sequence G. The BWT of G can be computed immediately from the suffix array of G, and the suffix array of the reference genome sequence G can be efficiently computed using a known method as described in Embodiment 1 (Non Patent Literature 8). In addition, it is well known that when a place where the base sequence s appears as a partial sequence of G is unique, the position coordinate of the base sequence can be efficiently computed using the BWT of G (Non Patent Literature 7).

Figure 15:
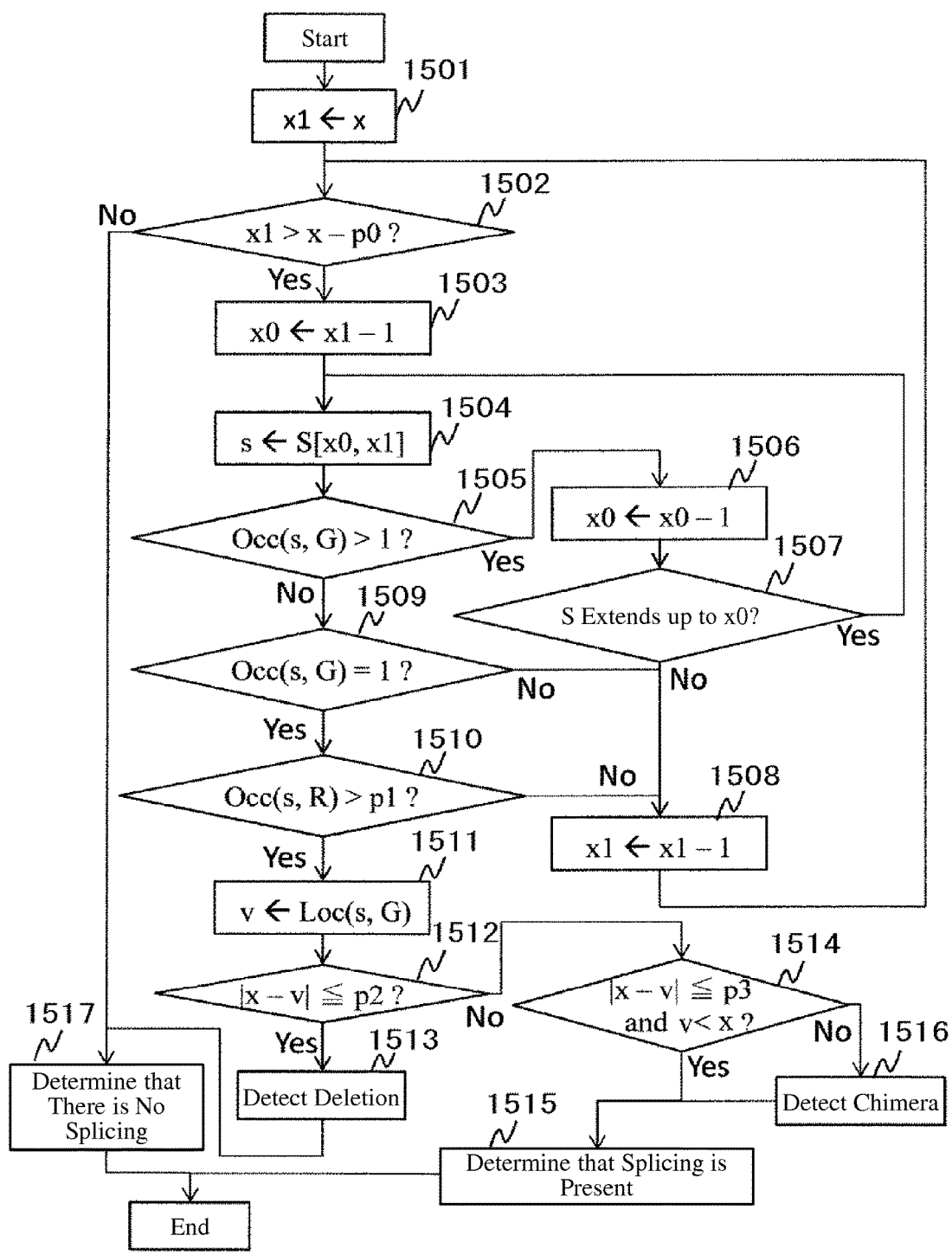
FIG. 15 is a flowchart showing a method for determining the presence or absence of splicing by comparing a common sequence S of read sequences with a genome sequence in accordance with Embodiment 2.

FIG. 15 is a flowchart showing a method for determining the presence or absence of splicing at the position x by comparing the common sequence S of the read sequences with the genome sequence around x in this embodiment. Herein, symbols p0, p1, p2, and p3 are determination reference parameters indicated by a user. First, a variable x1 is initially set to a position coordinate x estimated to contain splicing (1501). X1 and x are compared (1502), and if the two has a difference of p0 or more, it is determined that there is no splicing, and the process is terminated (1517). Otherwise, the value of x0 is updated (1503), and the partial sequence s of S is determined (1504). The depth Occ(s, G) of s in the genome sequence data is computed (1505), and if the depth is greater than 1, the process proceeds to a process (1506) of updating x0. Otherwise, if Occ(s, G) is equal to 1 (1509), and if the depth Occ(s, R) of s in the read sequence data is greater than p1 (1510), the process proceeds to 1511. Meanwhile, if Occ(s, G) is zero (1509) or if Occ(s, R) is less than or equal to p1 (1510), the process proceeds to a process (1508) of updating x1, and then, the process returns to the process (1502) of comparing x1 and x, and the process is continued. After the process (1506) of updating x0, whether the common sequence S has been determined for the range of up to x0 is determined. If so, the process returns back to 1504 to update s, and the process is continued.

Otherwise, the process proceeds to the process 1508 of updating x1, and the process is continued. If the process proceeds to 1511, the position v at which s uniquely appears is determined, and if the distance from x to v is less than or equal to p2, it is determined that short deletion with a length of less than or equal to p2 is detected (1513), and thus, it is determined that there is no splicing (1517) and the process is terminated. Otherwise, if v is located to the left of x and the distance from x to v is less than or equal to p3 (1514), splicing is determined to be present, and the process is terminated (1515). Otherwise, it is determined that a chimeric gene (i.e., fusion gene) is detected (1516), and splicing is thus determined to be present (1515), and the process is terminated.

Figure 16:
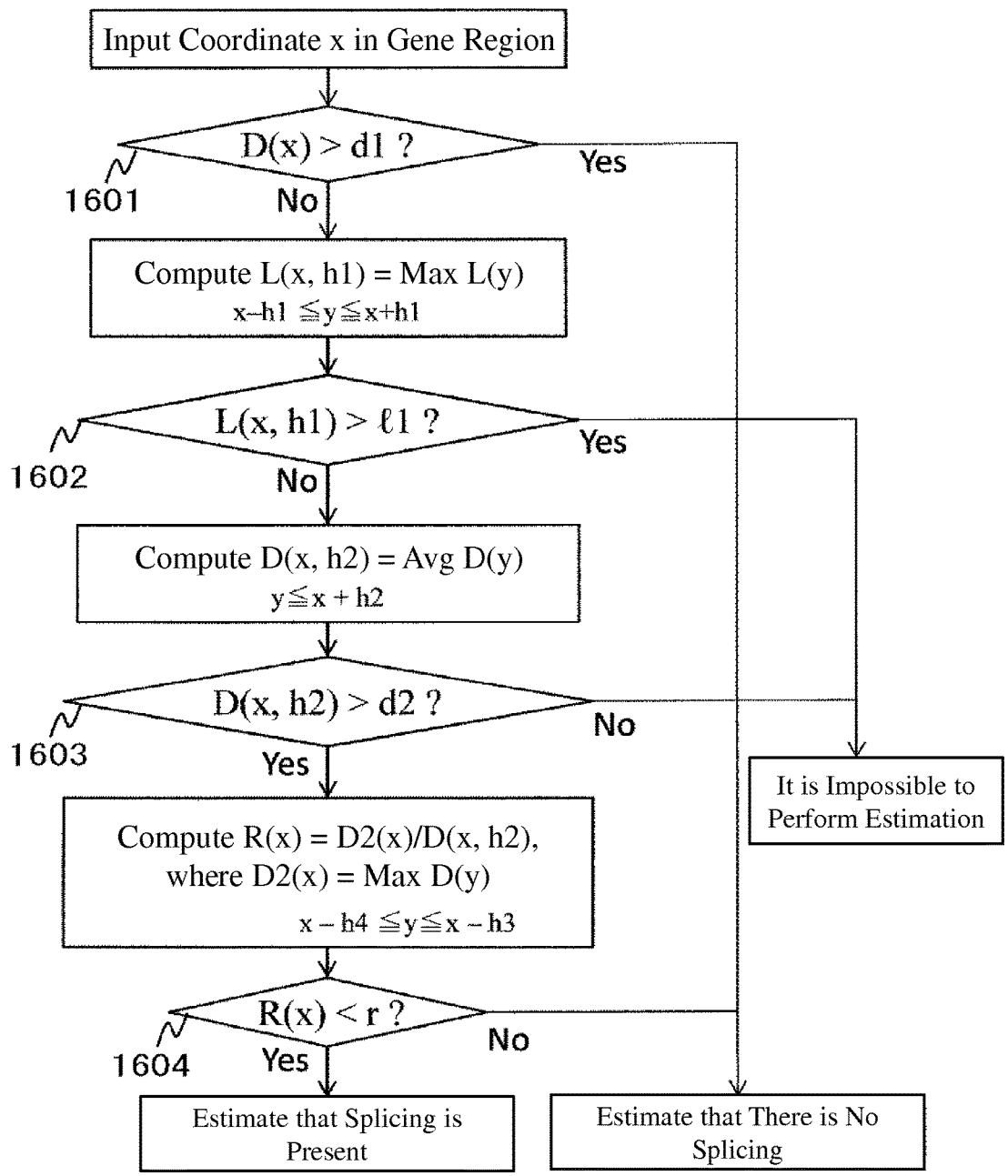
FIG. 16 is a flowchart showing a method for estimating the presence or absence of splicing at the genome coordinate x on the basis of the MLU and the depth by performing a search in the forward direction in accordance with Embodiment 2.

FIG. 16 is a flowchart showing a method for estimating the presence or absence of splicing at the base position x on the basis of the MLU and the depth by performing a search in the forward direction in this embodiment. Regarding each base position y around x, inclusive of x, it is assumed that the values of the MLU and the depth, that is, the values L(y) and D(y) have been acquired as a result of inquiring of the genome sequence DB and the read sequence DB. Symbols d1, d2, h1, h2, h3, h4, and l1 are estimation reference parameters. Such values are input before starting the process. If the depth D(x) is sufficiently large at the position x, it is estimated that there is no splicing (1601). If the MLU is large in the neighboring region of x, it is estimated that estimation cannot be performed (1602). If the average depth in the neighboring region of x on the forward direction side is not sufficiently large, it is estimated that estimation cannot be performed (1603). If the depth is significantly smaller in the neighboring region of x on the backward direction side than in the neighboring region of x on the forward direction side, splicing is estimated to be present. Otherwise, splicing is estimated to be absent (1604).

In the present invention described above, a process of inspecting a mapping destination by taking into consideration a variety of possible sequencing errors for each read sequence is not performed at all. That is, for the read sequence data, a process of sorting all suffixes thereof (inclusive of the read sequence data) in the lexicographic order is merely performed. Such a sorting process is simple, not involving using one's discretion. Thus, as a bias that depends on the processing method is not generated, a neutral process is possible. Further, as the process is simple, the computational cost can be suppressed as compared to that for a mapping process.

In addition, computation of the MLU on the reference genome side and the process of sorting all suffixes on the read sequence side are performed totally independently of each other. Therefore, when a plurality of reference genome sequences are prepared, it is not necessary to perform a process that depends on combinations of the reference genome sequences and read sequences.

Further, in the downstream process of analyzing variations, it is possible to estimate a region that has a high possibility of containing variations by inquiring of the reference genome sequence database (about the MLU or a partial sequence with a length of the MLU) and inquiring of the read sequence database (about the depth for a key sequence or read sequences that contain the key sequence), and performing a detailed analysis by narrowing down all read sequences to a target read sequence. Thus, according to the present invention, it is possible to efficiently analyze variations by narrowing down a target without performing a conventional mapping process.

It should be noted that the present invention is not limited to the aforementioned embodiments, and includes a variety of variations. For example, although the aforementioned embodiments have been described in detail for better understanding of the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add/remove/substitute a configuration of another embodiment.

Further, although an example has been described in which a program for implementing some or all of the aforementioned configurations, functions, processing units, and the like is created, it is needless to mention that some or all of them may also be implemented by hardware by designing integrated circuits.

REFERENCE SIGNS LIST

100, 122 User terminal
101 DNA Sample
102 Massively parallel DNA sequencer
103 Read sequence data
104 Read sequence database (DB) creating process
105 Read sequence database (DB)
106 Reference genome sequence data
107 Genome sequence database (DB) creating process
108 Genome sequence database (DB)
123 Disk
407 Sorted list of cyclic permutations (SLCP)
408 BWT of read sequence data
501 Sorted list of cyclic permutations (SLCP)
1104 Binary coded data of MLU (minimum length for uniqueness) of genome sequence
1700 Analysis device 1701 Processing unit (CPU)
1702 Memory
1703 Display unit
1704 Storage Device (HDD)
1705 Input unit
1706 Network interface (NIF)
1707 Bus

The invention claimed is:

1. A data analysis device comprising:
at least one storage medium configured to store a reference genome sequence database and a read sequence database, the genome sequence database including data representing a plurality of reference genome sequences and lengths at which partial sequences starting from base positions of the reference genome sequences become unique, and the read sequence database including data representing a Burrows-Wheeler Transform (BWT) of a plurality of read base sequences and a plurality of integer values representing a plurality of predetermined head bases of a sorted list of cyclic permutations (SLCP) corresponding to the read base sequences; and
a processor programmed to:
select a key sequence on the basis of a specified genome region to be analyzed, the key sequence being a partial sequence with a length of a first minimum length for uniqueness (MLU) in the specified genome region which is determined by referring to the genome sequence database,
determine a depth of the key sequence by referring to the BWT and the integer values of the head bases of the SLCP of the read sequence database, the depth being a number of the read base sequences that contain the key sequence,
scan the specified genome region and estimate a position by referring to the read sequence database based on the first MLU and the determined depth of the key sequence,
acquire a partial gene sequence with a second MLU from the estimated position,
extract the read base sequences containing the partial gene sequence at the estimated position from the read sequence database,
compare the extracted read base sequences with the reference genome sequences to analyze the specified genome region, and
output a result of the analysis.

2. The data analysis device according to claim 1, wherein the processor is programmed, for each coordinate in the specified genome region, to:
determine the first MLU at which a partial sequence becomes unique in the reference genome sequences for the respective coordinate, and
select, as the key sequence, the partial sequence with the length of the first MLU for the respective coordinate,
determine the depth of the key sequence by referring to the BWT and the integer values of the head bases of the SLCP of the read sequence database for the respective coordinate,
scan the specified genome region and estimate the position from the respective coordinate by referring to the read sequence database based on the first MLU and the determined depth of the key sequence for the respective coordinate,
acquire a partial gene sequence with a second MLU from the estimated position for the respective coordinate,
extract the read base sequences containing the partial gene sequence at the estimated position from the read sequence database for the respective coordinate,
compare the extracted read base sequences with the reference genome sequences to analyze the respective coordinate of the specified genome region, and
output a result of the comparison for the respective coordinate.

3. The data analysis device according to claim 1, wherein the processor is programmed to:
estimate the position at which the determined depth of the key sequence is locally small in the read sequence database as a position at which a possibility of a variation having occurred is high, and
compare the extracted read base sequences with the reference genome sequences to analyze the variation.

4. The data analysis device according to claim 1, wherein the processor is programmed to:
estimate the position at which the determined depth of the key sequence is locally smaller in a rear region than in a front region in the read sequence database as a position at which a possibility of splicing having occurred is high, and
compare the extracted read base sequences with the reference genome sequences to analyze the splicing.

5. The data analysis device according to claim 1, wherein the processor is programmed to:
receive one or more estimation reference parameters,
wherein the estimated position is determined based on the one or more estimation reference parameters.

6. The data analysis device according to claim 5, wherein the processor is programmed to:
estimate the position at which the depth of the key sequence is locally small in the read sequence database as a position at which a possibility of a variation having occurred is high based on the one or more estimation reference parameters, and
compare the extracted read base sequences with the reference genome sequences to analyze the variation.

7. The data analysis device according to claim 5, wherein the processor is programmed to:
estimate the position at which the depth of the key sequence is locally smaller in a rear region than in a front region in the read sequence database as a position at which a possibility of splicing having occurred is high based on the one or more estimation reference parameters, and
compare the extracted read base sequences with the reference genome sequences to analyze the splicing.

8. The data analysis device according to claim 1, further comprising:
a display unit configured to display the output result from the processor.

9. A DNA analysis method performed by a processor, the DNA analysis method comprising:
providing a reference genome sequence database and a read sequence database, the genome sequence database including data representing a plurality of reference genome sequences and lengths at which partial sequences starting from base positions of the reference genome sequences become unique, and the read sequence database including data representing a Burrows-Wheeler Transform (BWT) of a plurality of read base sequences and a plurality of integer values representing a plurality of predetermined head bases of a sorted list of cyclic permutations (SLCP) corresponding to the read base sequences;

selecting a key sequence on the basis of a specified genome region to be analyzed, the key sequence being a partial sequence with a length of a first minimum length for uniqueness (MLU) in the specified genome region which is determined by referring to the genome sequence database;

determining a depth of the key sequence by referring to the BWT and the integer values of the head bases of the SLCP of the read sequence database, the depth being a number of the read base sequences that contain the key sequence;

scanning the specified genome region and estimating a position by referring to the read sequence database based on the first MLU and the determined depth of the key sequence;

acquiring a partial gene sequence with a second MLU from the estimated position;

extracting the read base sequences containing the partial gene sequence at the estimated position from the read sequence database;

comparing the extracted read base sequences with the reference genome sequences to analyze the specified genome region; and outputting a result of the analysis.

10. The DNA analysis method according to claim 9, wherein:

the first MLU at which a partial sequence becomes unique is respectively determined in the reference genome sequences for each coordinate in the specified genome region, the key sequence is respectively selected for each coordinate in the specified genome region, the depth of the key sequence is respectively determined by referring to the BWT and the integer values of the head bases of the SLCP of the read sequence database for each coordinate in the specified genome region, the position from each coordinate in the specified genome region is respectively estimated by referring to the read sequence database based on the first MLU and the determined depth of the key sequence for the respective coordinate, a partial gene sequence with a second MLU from the estimated position is respectively acquired for each coordinate in the specified genome region, the read base sequences containing the partial gene sequence at the estimated position is respectively acquired from the read sequence database for each coordinate in the specified genome region, the extracted read base sequences are respectively compared with the reference genome sequences for each coordinate in the specified genome region to analyze the coordinates of the specified genome region, and the result of the comparison is output for each coordinate in the specified genome region.

11. The DNA analysis method according to claim 9, wherein:

the estimated position is a position at which the depth of the key sequence is locally small in the read sequence database and indicates that a possibility of a variation having occurred is high, and the extracted read base sequences are compared with the reference genome sequences to analyze the variation.

12. The DNA analysis method according to claim 9, wherein:

the estimated position is a position at which the depth of the key sequence is locally smaller in a rear region than in a front region in the read sequence database and indicates that a possibility of splicing having occurred is high, and the extracted read base sequences are compared with the reference genome sequences to analyze the splicing.

13. The DNA analysis method according to claim 9, further comprising:

receiving one or more estimation parameters, wherein the estimated position is determined based on the one or more estimation reference parameters.

14. The DNA analysis method according to claim 13, wherein:

the estimated position is a position at which the depth of the key sequence is locally small in the read sequence database and indicates that a possibility of a variation having occurred is high based on the one or more estimation reference parameters, and the extracted read base sequences are compared with the reference genome sequences to analyze the variation.

15. The DNA analysis method according to claim 13, wherein:

the estimated position is a position at which the depth of the key sequence is locally smaller in a rear region than in a front region in the read sequence database and indicates that a possibility of splicing having occurred is high based on the one or more estimation reference parameters, and the extracted read base sequences are compared with the reference genome sequences to analyze the splicing.

16. A non-transitory computer readable storage medium for DNA analysis comprising:

code for providing a reference genome sequence database and a read sequence database, the genome sequence database including data representing a plurality of reference genome sequences and lengths at which partial sequences starting from base positions of the reference genome sequences become unique, and the read sequence database including data representing a Burrows-Wheeler Transform (BWT) of a plurality of read base sequences and a plurality of integer values representing a plurality of predetermined head bases of a sorted list of cyclic permutations (SLCP) corresponding to the read base sequences;

code for selecting a key sequence on the basis of a specified genome region to be analyzed, the key sequence being a partial sequence with a length of a first minimum length for uniqueness (MLU) in the specified genome region which is determined by referring to the genome sequence database;

code for determining a depth of the key sequence by referring to the BWT and the integer values of the head bases of the SLCP of the read sequence database, the depth being a number of the read base sequences that contain the key sequence;

code for scanning the specified genome region and estimating a position by referring to the read sequence database based on the first MLU and the determined depth of the key sequence, code for acquiring a partial gene sequence with a second MLU from the estimated position, code for extracting the read base sequences containing the partial gene sequence at the estimated position from the read sequence database, code for comparing the extracted read base sequences with the reference genome sequences to analyze the specified genome region, and code for outputting a result of the analysis.

17. The non-transitory computer readable storage medium according to claim 16, wherein the comparison determines a variation in the specified genome region.

18. The non-transitory computer readable storage medium according to claim 16, wherein the comparison determines a splicing in the specified genome region.

* * * * *